(12) United States Patent
Bhalla et al.

(10) Patent No.: US 11,511,923 B2
(45) Date of Patent: Nov. 29, 2022

(54) CARTRIDGE PACKAGING FOR VAPORIZER CARTRIDGES

(71) Applicant: JUUL Labs, Inc., San Francisco, CA (US)

(72) Inventors: Rajeev Bhalla, Palo Alto, CA (US); Jason C. Curtis, Alameda, CA (US); Peter C. De Alva, Lake Zurich, IL (US); PyiPhyo Lwin, Newark, CA (US); Kevin J. Myers, San Jose, CA (US); Alexander J. Parker, Berkeley, CA (US); Vincent C. Phua, Piedmont, CA (US); Alexandra N. Siano, San Francisco, CA (US); Srinivasan Sundararajan, Cupertino, CA (US); Jambunathan Vangal Ramamurthy, San Jose, CA (US); Thomas J. White, Pebble Beach, CA (US)

(73) Assignee: JUUL Labs, Inc., San Francisco, CA (US)

( * ) Notice: Subject to any disclaimer, the term of this patent is extended or adjusted under 35 U.S.C. 154(b) by 510 days.

(21) Appl. No.: 16/273,102

(22) Filed: Feb. 11, 2019

(65) Prior Publication Data
US 2020/0130911 A1 Apr. 30, 2020

Related U.S. Application Data

(60) Provisional application No. 62/752,885, filed on Oct. 30, 2018.

(51) Int. Cl.
*B65D 75/36* (2006.01)
*A61M 11/04* (2006.01)

(52) U.S. Cl.
CPC ......... *B65D 75/367* (2013.01); *A61M 11/042* (2014.02)

(58) Field of Classification Search
CPC ..... A24F 7/008; A24F 47/008; B65D 75/367; B65D 75/527; B65D 75/366; B65D 75/36;
(Continued)

(56) References Cited

U.S. PATENT DOCUMENTS 2,745,751 A 5/1956 Pichardo
3,053,383 A 9/1962 Kahn
(Continued)

FOREIGN PATENT DOCUMENTS

FR 2188569 A5 1/1974
JP 1255046 9/2005
(Continued)

*Primary Examiner* — Chun Hoi Cheung
(74) *Attorney, Agent, or Firm* — Mintz Levin Cohn Ferris Glovsky and Popeo, P.C.

(57) ABSTRACT

Cartridge packaging for nicotine delivery systems are provided. Various embodiments of cartridge packaging are described that include or use one or more perforations or perforating patterns separating the cartridges. In one embodiment, for example, a cartridge pack can include a plurality of cartridge pack cavities that are each configured to receive a vaporizer cartridge and separated by a vertical perforation region, and a void cavity separated from the plurality of cartridge pack cavities by a horizontal perforation region. Related systems, methods, and articles of manufacture are also described.

21 Claims, 13 Drawing Sheets

(58) Field of Classification Search
CPC .............................. B65D 75/52; B65D 83/10; B65D 2575/3245; B65D 83/04; B65D 75/566
USPC ........ 206/242–276, 557–567, 484, 528–540; 220/623, 625
See application file for complete search history.

(56) References Cited

U.S. PATENT DOCUMENTS

| | | | |
|---|---|---|---|
| 4,196,809 A * | 4/1980 | Tonrey | B65D 77/2064 206/534 |
| D256,777 S | 9/1980 | Sorsjo | |
| 4,398,634 A * | 8/1983 | McClosky | B65D 75/323 206/484 |
| D294,459 S | 3/1988 | Wendel | |
| 4,812,067 A | 3/1989 | Brown et al. | |
| 4,899,976 A * | 2/1990 | Cederroth | F25C 1/243 249/61 |
| D342,025 S | 12/1993 | Abraben et al. | |
| 5,310,060 A * | 5/1994 | Bitner | B65D 75/327 206/469 |
| 5,392,909 A | 2/1995 | Hackett | |
| D364,343 S | 11/1995 | Mello | |
| 5,593,036 A * | 1/1997 | Dyble | B65D 75/366 206/348 |
| 6,155,423 A * | 12/2000 | Katzner | B65D 75/327 206/469 |
| 6,230,894 B1 * | 5/2001 | Danville | B65D 75/327 206/469 |
| D494,857 S | 8/2004 | Chen et al. | |
| 6,830,153 B2 * | 12/2004 | French | B65D 75/327 206/538 |
| D525,879 S | 8/2006 | Ueda et al. | |
| 7,093,816 B2 * | 8/2006 | Lacan | F25C 1/243 249/61 |
| D548,110 S | 8/2007 | Pugh | |
| D556,601 S | 12/2007 | Ferguson et al. | |
| D590,246 S | 4/2009 | Kirk et al. | |
| D642,483 S | 8/2011 | Stuiber et al. | |
| 8,051,983 B2 * | 11/2011 | Simon | B65D 50/06 206/532 |
| D655,628 S | 3/2012 | Mehren et al. | |
| D665,250 S | 8/2012 | Kirk et al. | |
| D686,090 S | 7/2013 | Logue | |
| 8,499,936 B2 * | 8/2013 | Albrecht | B65D 83/0463 206/528 |
| D713,741 S | 9/2014 | Wilmers | |
| 8,925,726 B2 * | 1/2015 | Bergey | B65B 51/10 206/532 |
| D760,599 S | 7/2016 | Jayakaran et al. | |
| D761,124 S | 7/2016 | Taylor | |
| D763,706 S | 8/2016 | Shum et al. | |
| D792,222 S | 7/2017 | Sill et al. | |
| 9,963,265 B1 * | 5/2018 | Braverman | B65D 75/327 |
| 10,968,021 B2 * | 4/2021 | Kuwa | B65D 75/367 |
| 2005/0051453 A1 | 3/2005 | Schuler et al. | |
| 2005/0051459 A1 * | 3/2005 | Casanova | B65D 75/366 206/703 |
| 2006/0138016 A1 * | 6/2006 | Harper | A61J 1/035 206/532 |
| 2007/0012592 A1 * | 1/2007 | Bertsch | B65D 75/327 206/531 |
| 2007/0246395 A1 * | 10/2007 | Arnold | B65D 75/58 206/532 |
| 2007/0272586 A1 * | 11/2007 | Hession | B65D 83/0463 206/532 |
| 2007/0289893 A1 * | 12/2007 | Williams, Jr. | B65D 77/2056 206/531 |
| 2008/0093252 A1 * | 4/2008 | Hession | B65D 83/0463 206/531 |
| 2008/0289989 A1 * | 11/2008 | Kalvelage | B65D 75/367 206/531 |
| 2009/0134051 A1 | 5/2009 | Rapp et al. | |
| 2009/0139893 A1 * | 6/2009 | McGonagle | A61J 1/035 206/531 |
| 2012/0248005 A1 | 10/2012 | Bergey | |
| 2014/0053952 A1 | 2/2014 | Genosar | |
| 2014/0305834 A1 * | 10/2014 | Knutson | B65D 75/327 206/531 |
| 2015/0209530 A1 * | 7/2015 | White | A24D 1/20 128/200.23 |
| 2015/0368018 A1 * | 12/2015 | Broedsgaard | B65D 75/327 206/461 |
| 2016/0143808 A1 * | 5/2016 | Pattison | A61J 1/035 206/530 |
| 2016/0304260 A1 * | 10/2016 | Ahn | B65D 75/327 |
| 2018/0153769 A1 * | 6/2018 | Dey | B65D 75/367 |
| 2018/0162617 A1 * | 6/2018 | Popkin | B65D 75/5833 |
| 2018/0162618 A1 * | 6/2018 | Maruyama | B65B 9/04 |
| 2019/0337700 A1 | 11/2019 | Berman | |
| 2020/0377276 A1 * | 12/2020 | Michaud | B32B 27/308 |

FOREIGN PATENT DOCUMENTS

| | | |
|---|---|---|
| JP | 1467041 | 3/2013 |
| JP | 1472926 | 5/2013 |
| TW | D152851 | 4/2013 |
| WO | WO-98/43893 A1 | 10/1998 |
| WO | WO-9843893 A1 | 10/1998 |

* cited by examiner

CARTRIDGE PACKAGING FOR VAPORIZER CARTRIDGES

CROSS REFERENCE TO RELATED APPLICATION(S)

This patent application claims priority to U.S. Provisional Application No. 62/752,885, filed on Oct. 30, 2018 and entitled "Blister Packaging for Two-Pack Nicotine Delivery System with Perforations."

TECHNICAL FIELD

The subject matter described herein relates to vaporizer devices, including a disposable vaporizer cartridge and cartridge packaging configured for containing vaporizer cartridges.

BACKGROUND

Vaporizer devices, which can also be referred to as vaporizers, electronic vaporizer devices or e-vaporizer devices, can be used for delivery of an aerosol (or "vapor") containing one or more active ingredients by inhalation of the aerosol by a user of the vaporizing device. For example, electronic cigarettes, which may also be referred to as e-cigarettes, are a class of vaporizer devices that are typically battery powered and that may be used to simulate the experience of cigarette smoking, but without burning of tobacco or other substances.

In use of a vaporizer device, the user inhales an aerosol, commonly called vapor, which may be generated by a heating element that vaporizes (which generally refers to causing a liquid or solid to at least partially transition to the gas phase) a vaporizable material, which may be liquid, a solution, a solid, a wax, or any other form as may be compatible with use of a specific vaporizer device. The vaporizable material used with a vaporizer can be provided within a cartridge (e.g., a part of the vaporizer that contains the vaporizable material in a reservoir) that includes a mouthpiece (e.g., for inhalation by a user).

To receive the inhalable aerosol generated by a vaporizer device, a user may, in certain examples, activate the vaporizer device by taking a puff, by pressing a button, or by some other approach. A puff, as the term is generally used (and also used herein), refers to inhalation by the user in a manner that causes a volume of air to be drawn into the vaporizer device such that the inhalable aerosol is generated by a combination of vaporized vaporizable material with the air.

A typical approach by which a vaporizer device generates an inhalable aerosol from a vaporizable material involves heating the vaporizable material in a vaporization chamber (or a heater chamber) to cause the vaporizable material to be converted to the gas (or vapor) phase. A vaporization chamber generally refers to an area or volume in the vaporizer device within which a heat source (e.g., conductive, convective, and/or radiative) causes heating of a vaporizable material to produce a mixture of air and vaporized vaporizable material to form a vapor for inhalation by a user of the vaporization device.

In some vaporizer device embodiments, the vaporizable material can be drawn out of a reservoir and into the vaporization chamber via a wicking element (a wick). Such drawing of the vaporizable material into the vaporization chamber can be due, at least in part, to capillary action provided by the wick, which pulls the vaporizable material along the wick in the direction of the vaporization chamber. However, as vaporizable material is drawn out of the reservoir, the pressure inside the reservoir is reduced, thereby creating a vacuum and acting against the capillary action. This can reduce the effectiveness of the wick to draw the vaporizable material into the vaporization chamber, thereby reducing the effectiveness of the vaporization device to vaporize a desired amount of vaporizable material, such as when a user takes a puff on the vaporizer device. Furthermore, the vacuum created in the reservoir can ultimately result in the inability to draw all of the vaporizable material into the vaporization chamber, thereby wasting vaporizable material. As such, improved vaporization devices and/or vaporization cartridges that improve upon or overcome these issues is desired.

The term vaporizer device, as used herein consistent with the current subject matter, generally refers to portable, self-contained, devices that are convenient for personal use. Typically, such devices are controlled by one or more switches, buttons, touch sensitive devices, or other user input functionality or the like (which can be referred to generally as controls) on the vaporizer, although a number of devices that may wirelessly communicate with an external controller (e.g., a smartphone, a smart watch, other wearable electronic devices, etc.) have recently become available. Control, in this context, refers generally to an ability to influence one or more of a variety of operating parameters, which may include without limitation any of causing the heater to be turned on and/or off, adjusting a minimum and/or maximum temperature to which the heater is heated during operation, various games or other interactive features that a user might access on a device, and/or other operations.

Various vaporizable materials having a variety of contents and proportions of such contents can be contained in the cartridge. Some vaporizable materials, for example, may have a smaller percentage of active ingredients per total volume of vaporizable material, such as due to regulations requiring certain active ingredient percentages. As such, a user may need to vaporize a large amount of vaporizable material (e.g., compared to the overall volume of vaporizable material that can be stored in a cartridge) to achieve a desired effect.

Some cartridge packaging may be difficult or impossible to unseal individual cartridges for use. Additionally, current designs of cartridge packaging may result in leakage of vaporizable material from the vaporizer cartridge, such as when the cartridge packaging is being shipped or stored for retail distribution. Deformation, such as bowing, of the packaging may occur that can result in various issues, such as packaging issues and damage to vaporizer cartridges during shipping or storing. Some cartridge packaging may include a configuration that places the vaporizer cartridges perpendicular to the direction of gravity during storage, which can increase the chance of vaporizable material leakage.

SUMMARY

Aspects of the current subject matter relate to cartridge packaging for vaporizer cartridges.

A cartridge packaging for containing a plurality of cartridges for a vaporizer device is provided. The cartridge packaging may include a base, a first cartridge pack cavity, a second cartridge pack cavity, and a void cavity.

The base may include a top surface and may be defined by a vertical dimension and a horizontal dimension. A plurality of cartridge pack cavities may be formed on the top surface of the base. The plurality of cartridge pack cavities may include the first cartridge pack cavity and the second cartridge pack cavity.

The first cartridge pack cavity and the second cartridge pack cavity may be formed adjacently on the top surface of the base. The first cartridge pack cavity and the second cartridge pack cavity may be separated by a vertical perforation in the base. The first cartridge pack cavity may be separated from the second cartridge pack cavity by the vertical perforation in the base. The vertical perforation may be provided along at least part of the vertical dimension of the base. The vertical perforation and the horizontal perforation may allow for removal of a portion of the base and a cartridge pack cavity formed thereon. The vertical perforation and the horizontal perforation may allow for removal of a portion of the base and one of the plurality of cartridge pack cavities formed thereon.

Each of the plurality of cartridge pack cavities, including the first cartridge pack cavity and the second cartridge pack cavity, may be recessed from the base to form an interior section that is sized and configured to contain one cartridge of the plurality of cartridges. The interior section of at least one of the first cartridge pack cavity and the second cartridge pack cavity may have a squared shape. The interior section of at least one of the plurality of cartridge pack cavities may have a squared shape.

The void cavity may be formed on the top surface of the base adjacent and vertically to the plurality of cartridge pack cavities, including the first cartridge pack cavity and the second cartridge pack cavity. The void cavity may extend along the horizontal dimension of the base and across at least a portion of the plurality of cartridge pack cavities, including the first cartridge pack cavity and the second cartridge pack cavity. The void cavity may be separated from the plurality of cartridge pack cavities, including the first cartridge pack cavity and the second cartridge pack cavity, by a horizontal perforation provided along at least part of the horizontal dimension of the base. The void cavity may be formed to reduce bowing of the base at least in a direction up from the top surface of the base.

The cartridge packaging further may include a cover layer applied to the base opposite the top surface of the base. The cover layer may provide an airtight seal to at least the first cartridge pack cavity and the second cartridge pack cavity when applied to the base. The cover layer may include a breakable material that, when broken proximate the first cartridge pack cavity or the second cartridge pack cavity, allows release of a cartridge from being contained by either the first cartridge pack cavity or the second cartridge pack cavity. The cover layer may include a breakable material that, when broken allows release of a cartridge from may be contained by one of the plurality of cartridge pack cavities.

The cartridge packaging may further include a peel-off perforation proximate to each of the plurality of cartridge pack cavities, including the first cartridge pack cavity or the second cartridge pack cavity. The peel-off perforation may extend from the horizontal perforation to an edge of the base.

Another embodiment of cartridge packaging for containing a plurality of cartridges for a vaporizer device is provided. The cartridge packaging may include a base, a plurality of cartridge pack cavities, a void cavity, and a cover layer. The base may include a top surface and may be defined by a vertical dimension and a horizontal dimension. The plurality of cartridge pack cavities may be formed on the top surface of the base. Each of the plurality of cartridge pack cavities may be separated from another cartridge pack cavity by a vertical perforation in the base. The vertical perforation may be provided along at least part of the vertical dimension of the base. Each of the plurality of cartridge pack cavities may be recessed from the base to form an interior section that is sized and configured to contain one cartridge of the plurality of cartridges. The interior section of at least one of the plurality of cartridge pack cavities may have a squared shape.

The void cavity may be formed on the top surface of the base adjacent and vertically to the plurality of cartridge pack cavities. The void cavity may extend along the horizontal dimension of the base and across at least a portion of the plurality of cartridge pack cavities. The void cavity may be separated from the plurality of cartridge pack cavities by a horizontal perforation provided along at least part of the horizontal dimension of the base. The void cavity may be formed to reduce bowing of the base at least in a direction up from the top surface of the base.

The cover layer may be applied to the base opposite the top surface. The cover layer may provide an airtight seal to each of the plurality of cartridge pack cavities when applied to the base. The cover layer may include a breakable material that, when broken proximate one of the plurality of cartridge pack cavities, allows release of a cartridge from being contained by one of the plurality of cartridge pack cavities.

The cartridge packaging may further include a peel-off perforation proximate to each of the plurality of cartridge pack cavities. The peel-off perforation may extend from the horizontal perforation to an edge of the base. The vertical perforation and the horizontal perforation may allow for removal of a portion of the base and one of the plurality of cartridge pack cavities formed thereon.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1A:
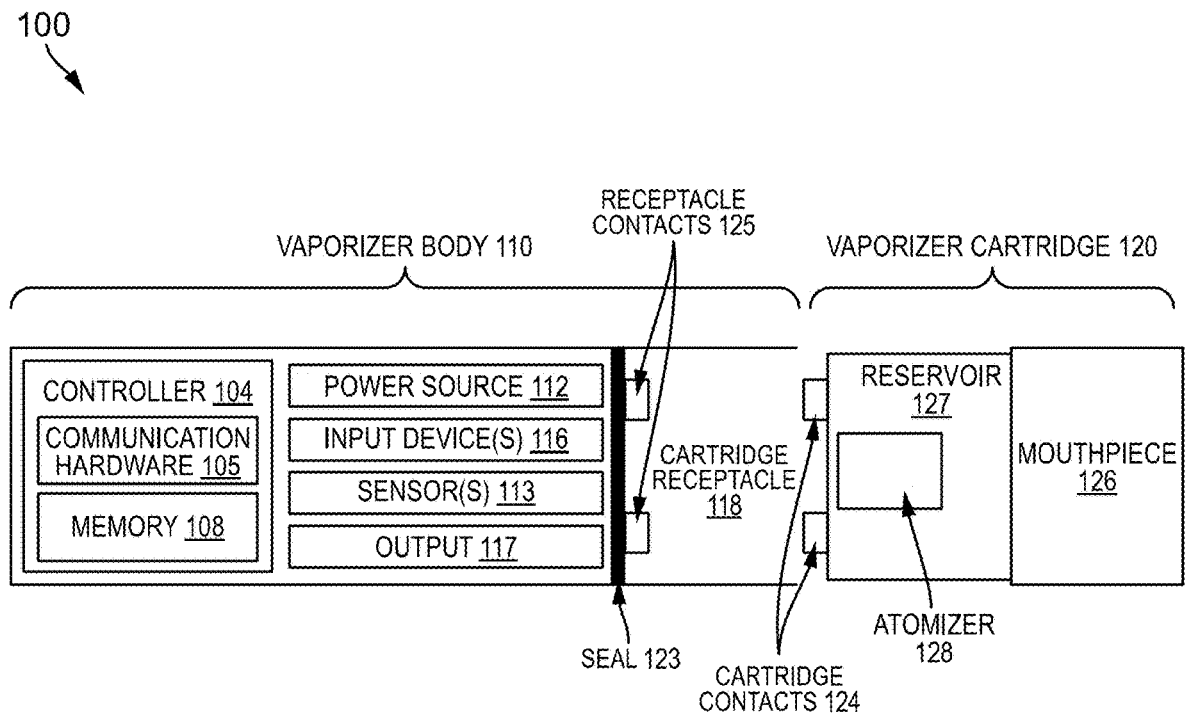
FIG. 1A illustrates a block diagram of a vaporizer consistent with implementations of the current subject matter.

Implementations of the current subject matter include devices relating to vaporizing of one or more materials for inhalation by a user. The term "vaporizer" is used generically in the following description to refer to a vaporizer device. Examples of vaporizers consistent with implementations of the current subject matter include electronic vaporizers, electronic cigarettes, e-cigarettes, or the like. Such vaporizers are generally portable, hand-held devices that heat a vaporizable material to provide an inhalable dose of the material.

The vaporizable material used with a vaporizer may optionally be provided within a cartridge (e.g., a part of the vaporizer that contains the vaporizable material in a reservoir or other container and that can be refillable when empty or disposable in favor of a new cartridge containing additional vaporizable material of a same or different type).

Various embodiments of a cartridge packaging for releasably storing one or more vaporizer cartridges are described herein. For example, the cartridge packaging may include a base having at least one cartridge pack cavity configured to contain a vaporizer cartridge. The cartridge packaging may also include a cover layer that can couple to the base and create a sealed storage compartment within each cavity. The cartridge packaging described herein may be hermetically sealed thereby protecting vaporizer cartridges against external factors, such as oxygen, humidity, and contamination.

For example, cartridge packaging may be manufactured using heat and pressure via a die to form the cartridge pack cavity from a sheet of formable material, such as a plastic material. Thermoforming methods of manufacturing can also be used to form the cartridge pack cavity. Advantages of plastic-based cartridge packs may include a more compact size as well as transparency to allow visualization of the cartridge contained within the cavity.

Bowing of cartridge packaging after thermoforming can result in potential packaging issues, such as during the carton insertion process (e.g., inserting the cartridge packaging into a storage carton). The cartridge packaging described herein may enable reduced bowing after thermoforming due to increased stress relief from one or more features as described in further detail below. Furthermore, the cartridge packaging described herein allows for compact packaging while achieving efficient and effective individual packaging of vaporizer cartridges. The cartridge packaging can also include features that allow individual vaporizer cartridges to be released from the packaging without disturbing sealed containment of other vaporizer cartridges of the same cartridge packaging.

Cartridge packaging can provide barrier protection for shelf life requirements, as well as prevent tampering of the cartridge and/or child resistance. In some embodiments, the cartridge packaging may individually seal each vaporizer cartridge, which can allow for improved protection against tampering of the vaporizer cartridges, as well as provide an indication as to any vaporizer cartridges that may have been tampered with. In some embodiments, the cartridge packaging may be opaque and protect against UV rays. In some embodiments, the cartridge packaging may be child resistant.

The cartridge packaging described herein may provide a cartridge packaging configuration that results in an orientation that does not place the vaporizer cartridges perpendicular to the direction of gravity, thereby decreasing the chance of vaporizable material leakage.

In some embodiments of the cartridge packaging, vaporizer cartridges may be contained between the cover layer and a cavity of the base. The base can be made out of a clear pre-formed plastic that allows a user to visually examine the vaporizer cartridge through the transparent plastic. In some embodiments, a portion of the base may be vacuum-formed around a mold that is sized and shaped similar to an embodiment of a vaporizer cartridge to which it is configured to contain. The base may be affixed to the cover layer using heat and pressure, which can allow an adhesive along the cover layer to secure (e.g., a heat seal coating) to the base. Vaporizer cartridges may be removed from the cartridge packaging by way of the cover layer. For example, the cover layer may be a push-through or peel-open foil that allows access to the vaporizer cartridge, such as by puncturing through the cover layer or peeling it back away from the base.

The cartridge packaging described herein may provide users with increased purchasing and usage options. For example, a user may separate individual packaged vaporizer cartridges without damage to other vaporizer cartridges in the same cartridge packaging.

The various embodiments of cartridge packaging described herein can provide a cost effective way of packaging, shipping, storing, and/or displaying vaporizer cartridges. Various embodiments of cartridge packaging are described in greater detail below.

In various implementations, a vaporizer may be configured for use with liquid vaporizable material (e.g., a carrier solution in which an active and/or inactive ingredient(s) are suspended or held in solution or a neat liquid form of the vaporizable material itself) or a solid vaporizable material. A solid vaporizable material may include a plant material that emits some part of the plant material as the vaporizable material (e.g., such that some part of the plant material remains as waste after the vaporizable material is emitted for inhalation by a user) or optionally can be a solid form of the vaporizable material itself (e.g., a "wax") such that all of the solid material can eventually be vaporized for inhalation. A liquid vaporizable material can likewise be capable of being completely vaporized or can include some part of the liquid material that remains after all of the material suitable for inhalation has been consumed.

Referring to the block diagram of FIG. 1A, a vaporizer device 100 typically includes a power source 112 (such as a battery which may be a rechargeable battery), and a controller 104 (e.g., a processor, circuitry, etc. capable of executing logic) for controlling delivery of heat to an atomizer 128 to cause a vaporizable material to be converted from a condensed form (e.g., a solid, a liquid, a solution, a suspension, a part of an at least partially unprocessed plant material, etc.) to the gas phase. The controller 104 may be part of one or more printed circuit boards (PCBs) consistent with certain implementations of the current subject matter.

After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which can form some or all of an inhalable dose provided by the vaporizer device 100 for a given puff or draw on the vaporizer. It will be understood that the interplay between gas and condensed phases in an aerosol generated by a vaporizer can be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc. may affect one or more physical parameters of an aerosol. In some vaporizers, and particularly for vaporizers for delivery of more volatile vaporizable materials, the inhalable dose may exist predominantly in the gas phase (i.e., formation of condensed phase particles may be very limited).

Vaporizers for use with liquid vaporizable materials (e.g., neat liquids, suspensions, solutions, mixtures, etc.) typically include an atomizer 128 in which a wicking element (also referred to herein as a wick (not shown in FIG. 1A), which can include any material capable of causing fluid motion by capillary pressure) conveys an amount of a liquid vaporizable material to a part of the atomizer that includes a heating element (also not shown in FIG. 1A). The wicking element is generally configured to draw liquid vaporizable material from a reservoir configured to contain (and that may in use contain) the liquid vaporizable material such that the liquid vaporizable material may be vaporized by heat delivered from a heating element. The wicking element may also optionally allow air to enter the reservoir to replace the volume of liquid removed. In other words, capillary action pulls liquid vaporizable material into the wick for vaporization by the heating element (described below), and air may, in some implementations of the current subject matter, return to the reservoir through the wick to at least partially equalize pressure in the reservoir. Other approaches to allowing air back into the reservoir to equalize pressure are also within the scope of the current subject matter.

The heating element can be or include one or more of a conductive heater, a radiative heater, and a convective heater. One type of heating element is a resistive heating element, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer can include a heating element that includes resistive coil or other heating element wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below.

Certain vaporizers may also or alternatively be configured to create an inhalable dose of gas-phase and/or aerosol-phase vaporizable material via heating of a non-liquid vaporizable material, such as for example a solid-phase vaporizable material (e.g., a wax or the like) or plant material (e.g., tobacco leaves and/or parts of tobacco leaves) containing the vaporizable material. In such vaporizers, a resistive heating element may be part of or otherwise incorporated into or in thermal contact with the walls of an oven or other heating chamber into which the non-liquid vaporizable material is placed. Alternatively, a resistive heating element or elements may be used to heat air passing through or past the non-liquid vaporizable material to cause convective heating of the non-liquid vaporizable material. In still other examples, a resistive heating element or elements may be disposed in intimate contact with plant material such that direct conductive heating of the plant material occurs from within a mass of the plant material (e.g., as opposed to only by conduction inward form walls of an oven).

The heating element may be activated (e.g., a controller, which is optionally part of a vaporizer body as discussed below, may cause current to pass from the power source through a circuit including the resistive heating element, which is optionally part of a vaporizer cartridge as discussed below), in association with a user puffing (e.g., drawing, inhaling, etc.) on a mouthpiece 126 of the vaporizer to cause air to flow from an air inlet, along an airflow path that passes an atomizer (e.g., wicking element and heating element), optionally through one or more condensation areas or chambers, to an air outlet in the mouthpiece. Incoming air passing along the airflow path passes over, through, etc. the atomizer, where gas phase vaporizable material is entrained into the air. As noted above, the entrained gas-phase vaporizable material may condense as it passes through the remainder of the airflow path such that an inhalable dose of the vaporizable material in an aerosol form can be delivered from the air outlet (e.g., in a mouthpiece 126 for inhalation by a user).

Activation of the heating element may be caused by automatic detection of the puff based on one or more of signals generated by one or more sensors 113, such as for example a pressure sensor or sensors disposed to detect pressure along the airflow path relative to ambient pressure (or optionally to measure changes in absolute pressure), one or more motion sensors of the vaporizer, one or more flow sensors of the vaporizer, a capacitive lip sensor of the vaporizer; in response to detection of interaction of a user with one or more input devices 116 (e.g., buttons or other tactile control devices of the vaporizer device 100), receipt of signals from a computing device in communication with the vaporizer; and/or via other approaches for determining that a puff is occurring or imminent.

As alluded to in the previous paragraph, a vaporizer consistent with implementations of the current subject matter may be configured to connect (e.g., wirelessly or via a wired connection) to a computing device (or optionally two or more devices) in communication with the vaporizer. To this end, the controller 104 may include communication hardware 105. The controller 104 may also include a memory 108. A computing device can be a component of a vaporizer system that also includes the vaporizer device 100, and can include its own communication hardware, which can establish a wireless communication channel with the communication hardware 105 of the vaporizer device 100.

For example, a computing device used as part of a vaporizer system may include a general purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer can also include one or more output 117 features or devices for providing information to the user.

A computing device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, etc.), controlling nicotine delivery (e.g., switching between nicotine and non-nicotine vaporizable material, adjusting an amount of nicotine delivered, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g., games, social media communications, interacting with one or more groups, etc.) with other users, or the like. The terms "sessioning", "session", "vaporizer session," or "vapor session," are used generically to refer to a period devoted to the use of the vaporizer. The period can include a time period, a number of doses, an amount of vaporizable material, and/or the like.

In the example in which a computing device provides signals related to activation of the resistive heating element, or in other examples of coupling of a computing device with a vaporizer for implementation of various control or other functions, the computing device executes one or more computer instructions sets to provide a user interface and underlying data handling. In one example, detection by the computing device of user interaction with one or more user interface elements can cause the computing device to signal the vaporizer device 100 to activate the heating element, either to a full operating temperature for creation of an inhalable dose of vapor/aerosol. Other functions of the vaporizer may be controlled by interaction of a user with a user interface on a computing device in communication with the vaporizer.

The temperature of a resistive heating element of a vaporizer may depend on a number of factors, including an amount of electrical power delivered to the resistive heating element and/or a duty cycle at which the electrical power is delivered, conductive heat transfer to other parts of the electronic vaporizer and/or to the environment, latent heat losses due to vaporization of a vaporizable material from the wicking element and/or the atomizer as a whole, and convective heat losses due to airflow (e.g., air moving across the heating element or the atomizer as a whole when a user inhales on the electronic vaporizer). As noted above, to reliably activate the heating element or heat the heating element to a desired temperature, a vaporizer may, in some implementations of the current subject matter, make use of signals from a pressure sensor to determine when a user is inhaling. The pressure sensor can be positioned in the airflow path and/or can be connected (e.g., by a passageway or other path) to an airflow path connecting an inlet for air to enter the device and an outlet via which the user inhales the resulting vapor and/or aerosol such that the pressure sensor experiences pressure changes concurrently with air passing through the vaporizer device from the air inlet to the air outlet. In some implementations of the current subject matter, the heating element may be activated in association with a user's puff, for example by automatic detection of the puff, for example by the pressure sensor detecting a pressure change in the airflow path.

Typically, the pressure sensor (as well as any other sensors) can be positioned on or coupled (e.g., electrically or electronically connected, either physically or via a wireless connection) to the controller 104 (e.g., a printed circuit board assembly or other type of circuit board). To take measurements accurately and maintain durability of the vaporizer, it can be beneficial to provide a resilient seal 123 to separate an airflow path from other parts of the vaporizer. The seal 123, which can be a gasket, may be configured to at least partially surround the pressure sensor such that connections of the pressure sensor to internal circuitry of the vaporizer are separated from a part of the pressure sensor exposed to the airflow path. In an example of a cartridge-based vaporizer, the seal 123 may also separate parts of one or more electrical connections between a vaporizer body 110 and a vaporizer cartridge 120. Such arrangements of a seal 123 in a vaporizer device 100 can be helpful in mitigating against potentially disruptive impacts on vaporizer components resulting from interactions with environmental factors such as water in the vapor or liquid phases, other fluids such as the vaporizable material, etc. and/or to reduce escape of air from the designed airflow path in the vaporizer. Unwanted air, liquid or other fluid passing and/or contacting circuitry of the vaporizer can cause various unwanted effects, such as alter pressure readings, and/or can result in the buildup of unwanted material, such as moisture, the vaporizable material, etc. in parts of the vaporizer where they may result in poor pressure signal, degradation of the pressure sensor or other components, and/or a shorter life of the vaporizer. Leaks in the seal 123 can also result in a user inhaling air that has passed over parts of the vaporizer device containing or constructed of materials that may not be desirable to be inhaled.

A general class of vaporizers that have recently gained popularity includes a vaporizer body 110 that includes a controller 104, a power source 112 (e.g., battery), one more sensors 113, charging contacts, a seal 123, and a cartridge receptacle 118 configured to receive a vaporizer cartridge 120 for coupling with the vaporizer body through one or more of a variety of attachment structures. In some examples, vaporizer cartridge 120 includes a reservoir 127 for containing a liquid vaporizable material and a mouthpiece 126 for delivering an inhalable dose to a user. The vaporizer cartridge can include an atomizer 128 having a wicking element and a heating element, or alternatively, one or both of the wicking element and the heating element can be part of the vaporizer body. In implementations in which any part of the atomizer 128 (e.g., heating element and/or wicking element) is part of the vaporizer body, the vaporizer can be configured to supply liquid vaporizer material from a reservoir in the vaporizer cartridge to the atomizer part(s) included in the vaporizer body.

Cartridge-based configurations for vaporizers that generate an inhalable dose of a non-liquid vaporizable material via heating of a non-liquid vaporizable material are also within the scope of the current subject matter. For example, a vaporizer cartridge may include a mass of a plant material that is processed and formed to have direct contact with parts of one or more resistive heating elements, and such a vaporizer cartridge may be configured to be coupled mechanically and electrically to a vaporizer body the includes a processor, a power source, and electrical contacts for connecting to corresponding cartridge contacts for completing a circuit with the one or more resistive heating elements.

In vaporizers in which the power source 112 is part of a vaporizer body 110 and a heating element is disposed in a vaporizer cartridge 120 configured to couple with the vaporizer body 110, the vaporizer device 100 may include electrical connection features (e.g., means for completing a circuit) for completing a circuit that includes the controller 104 (e.g., a printed circuit board, a microcontroller, or the like), the power source, and the heating element. These features may include at least two contacts on a bottom surface of the vaporizer cartridge 120 (referred to herein as cartridge contacts 124) and at least two contacts disposed near a base of the cartridge receptacle (referred to herein as receptacle contacts 125) of the vaporizer device 100 such that the cartridge contacts 124 and the receptacle contacts 125 make electrical connections when the vaporizer cartridge 120 is inserted into and coupled with the cartridge receptacle 118. The circuit completed by these electrical connections can allow delivery of electrical current to the resistive heating element and may further be used for additional functions, such as for example for measuring a resistance of the resistive heating element for use in determining and/or controlling a temperature of the resistive heating element based on a thermal coefficient of resistivity of the resistive heating element, for identifying a cartridge based on one or more electrical characteristics of a resistive heating element or the other circuitry of the vaporizer cartridge, etc.

In some examples of the current subject matter, the at least two cartridge contacts and the at least two receptacle contacts can be configured to electrically connect in either of at least two orientations. In other words, one or more circuits necessary for operation of the vaporizer can be completed by insertion of a vaporizer cartridge 120 in the cartridge receptacle 118 in a first rotational orientation (around an axis along which the end of the vaporizer cartridge having the cartridge is inserted into the cartridge receptacle 118 of the vaporizer body 110) such that a first cartridge contact of the at least two cartridge contacts 124 is electrically connected to a first receptacle contact of the at least two receptacle contacts 125 and a second cartridge contact of the at least two cartridge contacts 124 is electrically connected to a second receptacle contact of the at least two receptacle contacts 125. Furthermore, the one or more circuits necessary for operation of the vaporizer can be completed by insertion of a vaporizer cartridge 120 in the cartridge receptacle 118 in a second rotational orientation such that the first cartridge contact of the at least two cartridge contacts 124 is electrically connected to the second receptacle contact of the at least two receptacle contacts 125 and the second cartridge contact of the at least two cartridge contacts 124 is electrically connected to the first receptacle contact of the at least two receptacle contacts 125. This feature of a vaporizer cartridge 120 being reversible insertable into a cartridge receptacle 118 of the vaporizer body 110 is described further below.

In one example of an attachment structure for coupling a vaporizer cartridge 120 to a vaporizer body, the vaporizer body 110 includes a detent (e.g., a dimple, protrusion, etc.) protruding inwardly from an inner surface the cartridge receptacle 118. One or more exterior surfaces of the vaporizer cartridge 120 can include corresponding recesses (not shown in FIG. 1A) that can fit and/or otherwise snap over such detents when an end of the vaporizer cartridge 120 inserted into the cartridge receptacle 118 on the vaporizer body 110. When the vaporizer cartridge 120 and the vaporizer body 110 are coupled (e.g., by insertion of an end of the vaporizer cartridge 120 into the cartridge receptacle 118 of the vaporizer body 110), the detent into the vaporizer body 110 may fit within and/or otherwise be held within the recesses of the vaporizer cartridge 120 to hold the vaporizer cartridge 120 in place when assembled. Such a detent-recess assembly can provide enough support to hold the vaporizer cartridge 120 in place to ensure good contact between the at least two cartridge contacts 124 and the at least two receptacle contacts 125, while allowing release of the vaporizer cartridge 120 from the vaporizer body 110 when a user pulls with reasonable force on the vaporizer cartridge 120 to disengage the vaporizer cartridge 120 from the cartridge receptacle 118.

Further to the discussion above about the electrical connections between a vaporizer cartridge and a vaporizer body being reversible such that at least two rotational orientations of the vaporizer cartridge in the cartridge receptacle are possible, in some vaporizers the shape of the vaporizer cartridge, or at least a shape of the end of the vaporizer cartridge that is configured for insertion into the cartridge receptacle may have rotational symmetry of at least order two. In other words, the vaporizer cartridge or at least the insertable end of the vaporizer cartridge may be symmetric upon a rotation of 180° around an axis along which the vaporizer cartridge is inserted into the cartridge receptacle. In such a configuration, the circuitry of the vaporizer may support identical operation regardless of which symmetrical orientation of the vaporizer cartridge occurs.

In some examples, the vaporizer cartridge, or at least an end of the vaporizer cartridge configured for insertion in the cartridge receptacle may have a non-circular cross section transverse to the axis along which the vaporizer cartridge is inserted into the cartridge receptacle. For example, the non-circular cross section may be approximately rectangular, approximately elliptical (e.g., have an approximately oval shape), non-rectangular but with two sets of parallel or approximately parallel opposing sides (e.g., having a parallelogram-like shape), or other shapes having rotational symmetry of at least order two. In this context, approximately having a shape, indicates that a basic likeness to the described shape is apparent, but that sides of the shape in question need not be completely linear and vertices need not be completely sharp. Rounding of both or either of edges or vertices of the cross-sectional shape is contemplated in the description of any non-circular cross section referred to herein.

The at least two cartridge contacts and the at least two receptacle contacts can take various forms. For example, one or both sets of contacts may include conductive pins, tabs, posts, receiving holes for pins or posts, or the like. Some types of contacts may include springs or other urging features to cause better physical and electrical contact between the contacts on the vaporizer cartridge and the vaporizer body. The electrical contacts may optionally be gold-plated, and/or can include other materials.

Figure 1B:
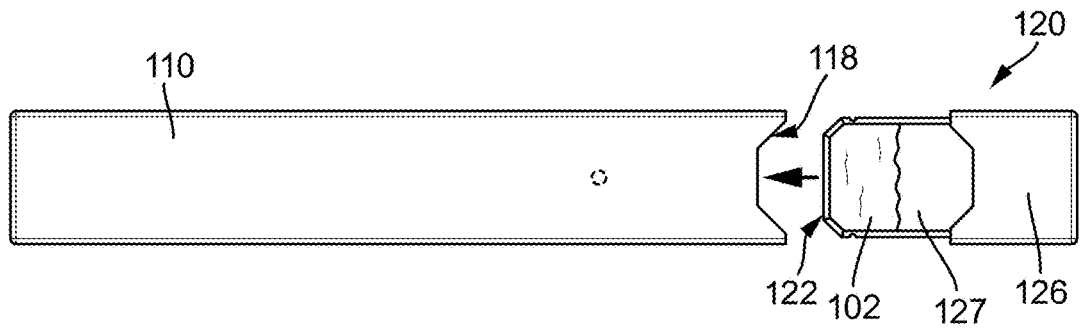
FIG. 1B illustrates a top view of an embodiment of the vaporizer of FIG. 1A showing a cartridge separated from a vaporizer device body.

FIG. 1B illustrates an embodiment of the vaporizer body 110 having a cartridge receptacle 118 into which the vaporizer cartridge 120 may be releasably inserted. FIG. 1B shows a top view of the vaporizer device 100 illustrating the cartridge being positioned for insertion into the vaporizer body 110. When a user puffs on the vaporizer device 100, air may pass between an outer surface of the vaporizer cartridge 120 and an inner surface of a cartridge receptacle 118 on the vaporizer body 110. Air can then be drawn into an insertable end 122 of the cartridge, through the vaporization chamber that includes or contains the heating element and wick, and out through an outlet of the mouthpiece 126 for delivery of the inhalable aerosol to a user. The reservoir 127 of the vaporizer cartridge 120 may be formed in whole or in part from translucent material such that a level of vaporizable material 102 is visible along the vaporizer cartridge 120.

Various embodiments of a cartridge packaging for releasably storing one or more vaporizer cartridges are described herein. The cartridge packaging includes a base coupled to a cover layer that is configured to secure at least one vaporizer cartridge therebetween. The base can include at least one cartridge pack cavity formed along a formable sheet. The base may be made from a formable material, such as a thermoformed plastic. The cartridge pack cavity may be configured to contain a vaporizer cartridge. Vaporizer cartridges may be removed from the cartridge pack cavity through the cover layer or as a result of the cover layer being removed. For example, the cover layer may be puncturable and/or configured to be peeled away from the base. As such, the vaporizer cartridge can be pushed through the cover layer or the cover layer can be peeled away from the base to allow the vaporizer cartridge to be released from the cavity, such as for use.

The cartridge packaging described herein may provide users with increased purchasing and usage options. For example, a user may separate individual packaged vaporizer cartridges without damage to other vaporizer cartridges in the same cartridge packaging.

The cartridge packaging described herein may include hermetic sealing which may be useful for protecting cartridges against external factors, such as oxygen, humidity, and contamination at least prior to use. Cartridge packaging can provide barrier protection for shelf life requirements, as well as a degree of tamper resistance, such as by individually sealing each vaporizer cartridge in a cartridge pack cavity. Cartridge packaging may provide configuration of vaporizer cartridges in an orientation that does not place the vaporizer cartridges perpendicular to the direction of gravity during storage, thereby decreasing the chance of vaporizable material leakage. Additionally, the cartridge packaging described herein can include a thickness that is the approximately the same as a width of the at least one vaporizer cartridge being contained therein, thereby minimizing packaging size for effective and efficient storage of vaporizer cartridges.

Various embodiments of cartridge packaging are described herein. For example, the cartridge packaging can vary in the number of vaporizer cartridges and/or cartridge pack cavities included per cartridge packaging, as well as the layout of each vaporizer cartridge and/or cartridge pack cavity relative to the other vaporizer cartridge and/or cartridge pack cavity. Cartridge packaging may be configured to house at least one vaporizer cartridge (e.g., 2, 3, 4, or more). Each individual vaporizer cartridge may be contained within a cartridge pack cavity of the base and covered by at least a portion of the cover layer.

As described above, the cartridge packaging can include a base including one or more cartridge pack cavities. For example, each cartridge pack cavity may include a depression along the base that is sized and shaped to contain an individual vaporizer cartridge. Further, cartridge pack cavities may be sized and shaped to provide a sliding fit with an outer surface of the vaporizer cartridge. The cartridge packaging can include a variety of shapes and sizes, such as rectangular, square, etc. The depth of the cartridge pack cavity can be approximately equivalent to a width of the vaporizer cartridge. For example, when the cover layer covers the cartridge pack cavity, the vaporizer cartridge can be maintained in an approximately stationary position within the cartridge pack cavity.

The cartridge packaging may include one or more perforations or holes between each cartridge pack cavity. Such perforations can be configured to separate each cartridge pack cavity of the cartridge packaging. For example, the perforations may be configured to separate a cartridge pack cavity from other cartridge pack cavities and/or the cartridge packaging while remaining sealed by a portion of the cover layer. The perforations can include a series of holes or slits thereby allowing for a more controlled and efficient tearing of the base (e.g., along the series of perforations). Perforations may allow for linear tearing of the base thereby releasing a cartridge pack cavity (and the vaporizer cartridge contained therein) from the base.

In some embodiments, the perforations may mitigate the occurrence of bowing or other deformation of the cartridge packaging. The cartridge packaging can also include regions of packaging that further mitigate the occurrence of deformation of the cartridge packaging, as will be described in greater detail below.

Figure 2A:
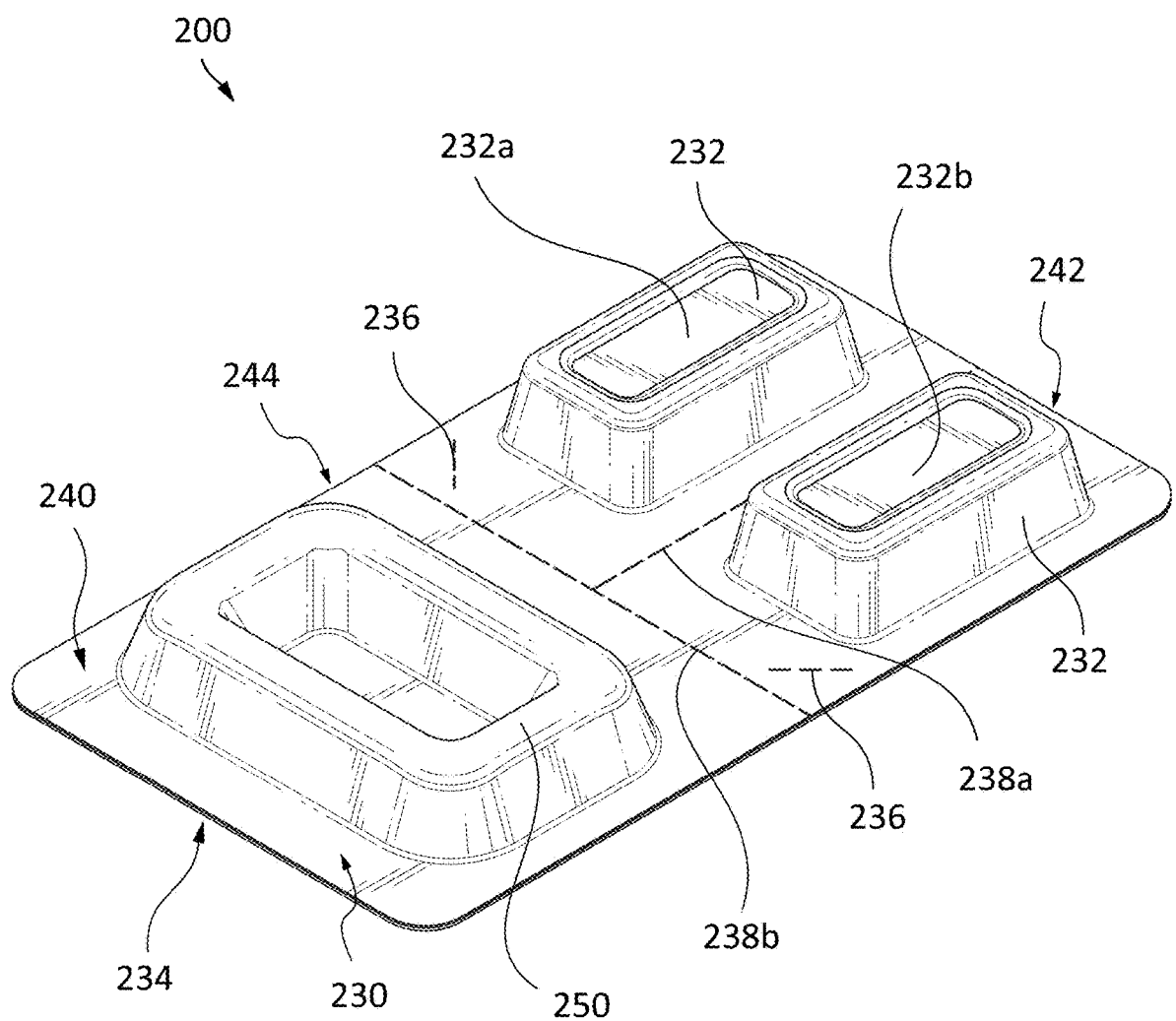
FIG. 2A illustrates a top perspective view of an embodiment of a two-pack cartridge packaging, consistent with implementations of the current subject matter.
Figure 2B:
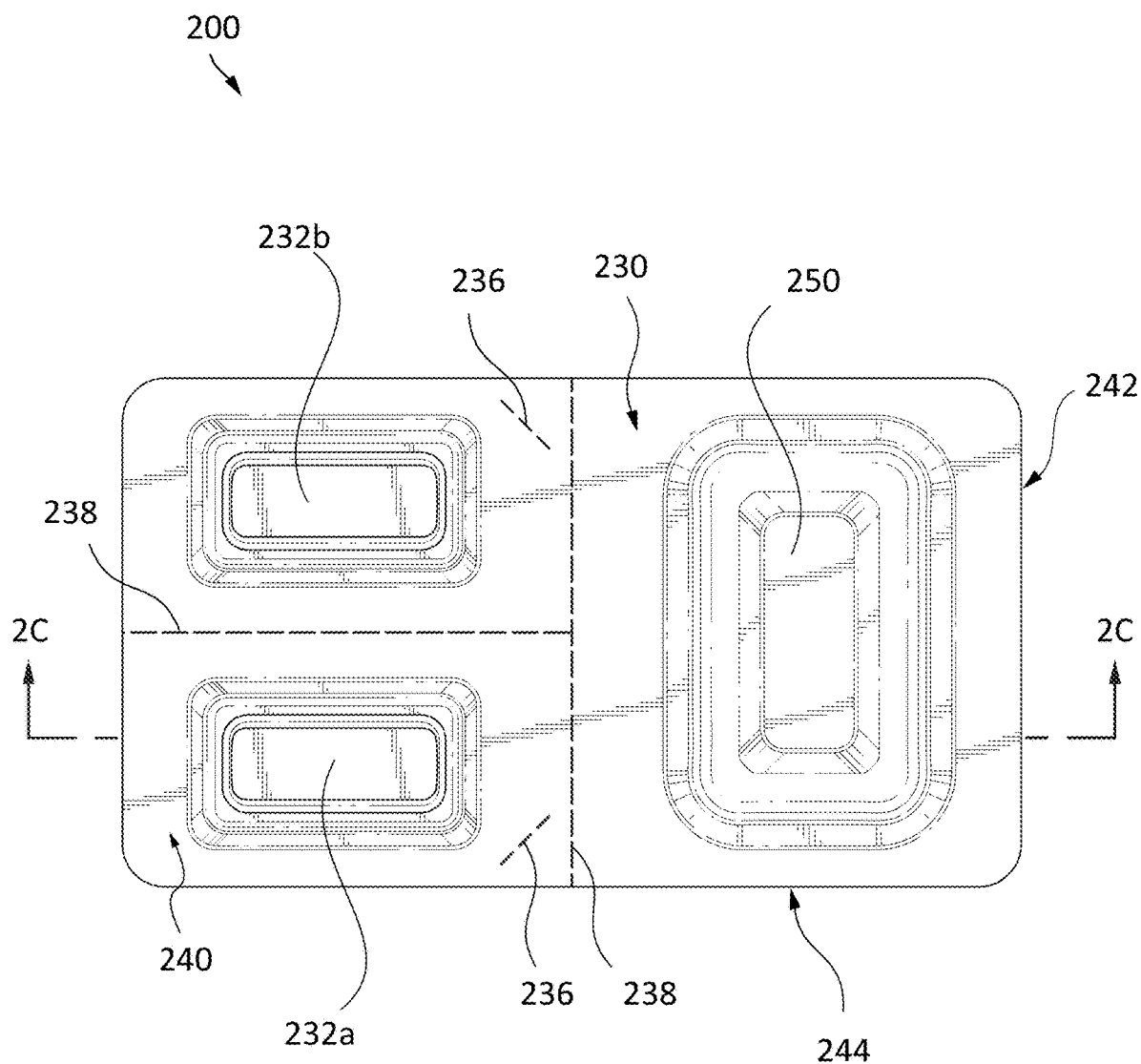
FIG. 2B illustrates a top view of the cartridge packaging embodiment of FIG. 2A.
Figure 2C:
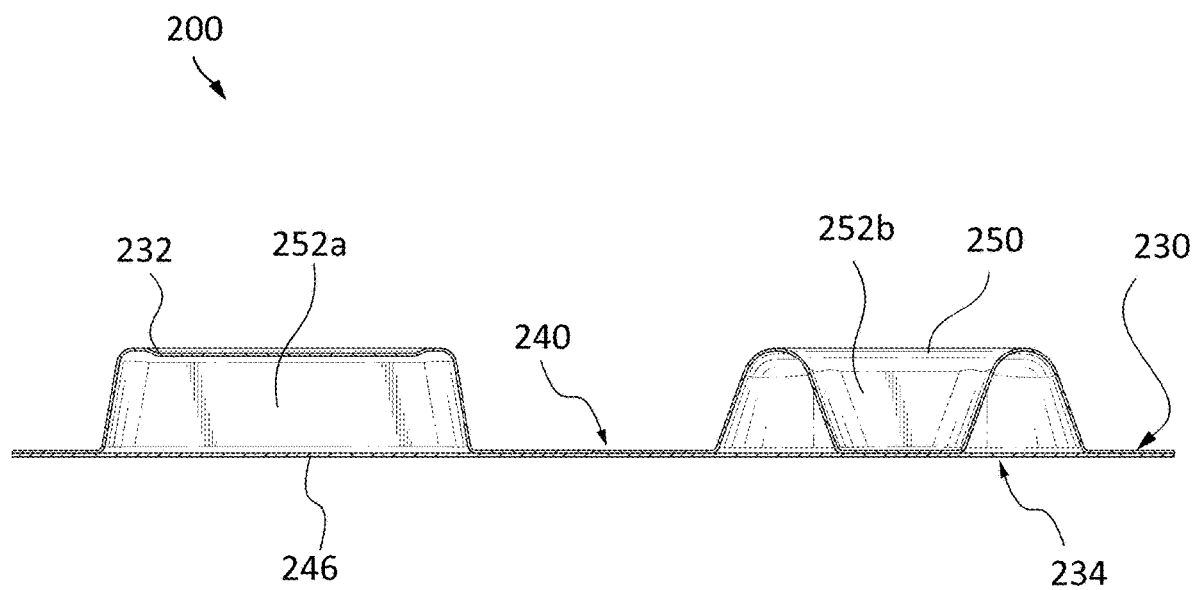
FIG. 2C illustrates a side cross-sectional view of the cartridge packaging embodiment of FIG. 2A.

FIGS. 2A-2C illustrate a first embodiment of a cartridge packaging 200 consistent with implementations of the current subject matter. In some implementations, the cartridge packaging 200 can include a base 230 having at least one cartridge pack cavity 232, such as a first cartridge pack cavity 232*a* and a second cartridge pack cavity 232*b*. In some implementations, the cartridge pack cavity 232 can be configured to hold a vaporizer cartridge, such as vaporizer cartridge 120 shown in FIGS. 1A and 1B. The cartridge pack cavity 232 can be formed in a variety of shapes and sizes to allow for containing various vaporizer cartridges. For example, the cartridge pack cavity 232 can include a squared shape, a circular shape, an oval shape, or other angular or rounded polyhedral shape. In some implementations, the base 230, including the first cartridge pack cavity 232*a* and the second cartridge pack cavity 232*b*, can be made from a laminated composite. In some implementations, the first cartridge pack cavity 232*a* and the second cartridge pack cavity 232*b* may vary in thickness. In some embodiments, a laminated composite forming the base material with various thicknesses may be used.

The cartridge packaging 200 can also include a cover layer 234 that is configured to adhere to the base 230, such as a bottom surface 246 of the base 230, and secure at least one vaporizer cartridge therebetween by creating a sealed storage compartment within the base 230. The cover layer 234 may be a push-through or peel-open configuration that allows access to the vaporizer cartridge, such as by puncturing through the cover layer 234 so the vaporizer cartridge can be pushed through the cover layer, or peeling the cover layer away from the base to allow the vaporizer cartridge to be accessed. The cover layer 234 can secure to a top side of the base 230 including openings to the at least one cartridge pack cavity 232. As such, each cartridge pack cavity 232 can securely contain a vaporizer cartridge.

In some implementations, the cartridge packaging 200 can include one or more peel-off perforation features 236 configured to facilitate the opening of a respective cartridge pack cavity 232, such as for releasing a vaporizer cartridge contained within the cartridge pack cavity 232. For example, the peel-off perforation features 236 delineate a region that can be can be lifted or bent back by a user to aid in tearing open or peeling back the cover layer 234 to access the vaporizer cartridge.

As shown in FIG. 2B, the first cartridge pack cavity 232a and the second cartridge pack cavity 232b can be substantially rectangular in shape. The first cartridge pack cavity 232a and the second cartridge pack cavity 232b may, in some implementations, have substantially the same or different dimensions.

As shown in FIG. 2A, the first cartridge pack cavity 232a and the second cartridge pack cavity 232b can be separated by one or more perforations 238, such as a vertical or first perforation 238a and a horizontal or second perforation 238b. The perforations 238 may be a row of small holes extending through the base and cover layer, as well as extending between each cartridge pack cavity 232, so that a single cartridge pack cavity 232 can be separated from other cartridge pack cavities while remaining sealed by the cover layer 234. The perforations 238 can allow for efficient and linear tearing of the base 230 thereby allowing the release of an individual cartridge pack cavity 232 (such as with the vaporizer cartridge contained therein) from the base 230. For example, the cartridge packaging may contain a continuous perforation that extends from the edges of the cartridge packaging around each individual vaporizer cartridge with a minimum seal border a thickness of approximately 2 mm to approximately 5 mm. The vertical perforation 238a may be perpendicular to the horizontal perforation 238b.

Further, bowing of cartridge packaging after thermoforming can result in potential packaging issues, such as during the carton insertion process (e.g., inserting the cartridge packaging into a carton for consumer packaging, shipping, and storage). Cartridge packaging 200 may minimize or eliminate bowing after thermoforming due to increased stress relief from one or more of the perforations 238, the peel-off perforation features 236, and/or other features.

The base 230 may be made out of a formable material, such as a thermoformed plastic, a polyvinyl chloride (PVC), and/or other materials. The cover layer 234 can be made out of a variety of materials, such as paper material, aluminum foil, and/or plastic. The cover layer 234 may be applied to a bottom surface 246 of the base 230 (e.g., the side including openings to the cartridge pack cavities) thereby creating an airtight seal securing the vaporizer cartridges into the cartridge packaging 200.

The top surface 240 of the base 230 may be defined by a vertical dimension 242 and a horizontal dimension 244. The first cartridge pack cavity 232a and the second cartridge pack cavity 232b may be separated by the vertical perforation 238a in the base 230. Additionally, the first cartridge pack cavity 232a may be separated from the second cartridge pack cavity 232b by the vertical perforation 238a in the base 230. The vertical perforation 238a may be provided along at least part of the vertical dimension 242 of the base 230. The vertical perforation 238a and the horizontal perforation 238b may allow for removal of a portion of the base 230 including a cartridge pack cavity 232 formed thereon. As shown in the current embodiment, the perforations 238 may be located on one half of the center axis of the short edge (e.g., vertical dimension 242) and along the entire center axis of the long edge (e.g., horizontal dimension 244). The vaporizer cartridges and cartridge pack cavities 232 may be oriented such that the long edge of each vaporizer cartridge is parallel to the long edge of the cartridge packaging 200.

The cartridge packaging as described herein may provide users with increased purchasing and usage options such as buying two vaporizer cartridges and separating one vaporizer cartridge at a time from the cartridge packaging. For example, cartridge packaging 200 provides a two-pack of vaporizer cartridges. By providing extra space and/or material to the cartridge packaging 200, a standardized carton size may be used to store cartridge packaging regardless if a two-pack of vaporizer cartridges, a four-pack of vaporizer cartridges, or other vaporizer cartridge quantities is being contained. Using a standardized carton may decrease manufacturing costs.

As shown in FIG. 2A, the cartridge packaging 200 can include a void cavity 250. The void cavity 250 may include a cavity or depression formed in the base 230 that is configured to remain empty and not contain a vaporizer cartridge therein. The void cavity 250 may be configured to provide a particular shape and/or orientation to the cartridge packaging 200 such that the vaporizable material held by the vaporizer cartridge in the cartridge pack cavity 232 does not leak. The void cavity 250 may provide structural integrity to the cartridge packaging 200 and may help to avoid damage to the cartridge packing 200 and/or carton during shipping and distribution by providing a void cavity 250 depression in the base 230 of a similar depth as the cartridge pack cavities 232, thus providing uniformity to the cartridge packaging 200 for insertion into the carton. The void cavity 250 may be a square, rectangle, taper inward, and/or other shapes. The void cavity 250 can be separated from the first cartridge pack cavity 232a and the second cartridge pack cavity 232b by the second, horizontal, perforation 238b. The first, vertical, perforation 238a and the second, horizontal, perforation 238b may include a series of small holes in the cover layer 234 or the base 230 made by boring or piercing.

The void cavity 250 may be formed along the base 230 such that an opening of the void cavity extends along the bottom surface 246 of the base 230. The void cavity 250 may be adjacent and vertically positioned relative to the plurality of cartridge pack cavities 232, including the first cartridge pack cavity 232a and the second cartridge pack cavity 232b. The void cavity 250 may extend along the horizontal dimension 244 of the base 230 such that the void cavity 250 extends along and adjacent to the first cartridge pack cavity 232a and the second cartridge pack cavity 232b, such as shown in FIG. 2B. The void cavity 250 may be separated from the plurality of cartridge pack cavities 232, including the first cartridge pack cavity 232a and the second cartridge pack cavity 232b, by a horizontal perforation 238b provided along at least part of the horizontal dimension 244 of the base 230. The void cavity 250 may be configured to reduce bowing of the base 230 at least in a direction up from the top surface 240 of the base 230. For example, the void cavity may have a size and shape that is the same or similar to the cartridge pack cavities but the void cavity is oriented differently compared to the cartridge pack cavities.

In some implementations, the void cavity 250 may be larger than the first cartridge pack cavity 232a and/or the second cartridge pack cavity 232b. In some implementations, the void cavity 250 may include a horizontal or linear structure that can extend from the base 230, such as in a same direction away from the bottom surface 246 of the base 230. In some implementations, the void cavity 250 can include a curvilinear (e.g., S-shaped, N-shaped, W-shaped, and the like) structure that can protrude from the base 230. Such structures can increase rigidity of the base thereby preventing bowing or bending of the base. Other void cavity 250 structural shapes are also contemplated.

The orientation of the vertical perforation 238a and horizontal perforation 238b can be an advantage of the current subject matter by the reduction of deformation of the base 230 after the cover layer 234 is applied to the base 230 during manufacturing of the cartridge-containing cartridge packaging. Furthermore, the design and the location of the void cavity 250 can, in some implementations, reduce the amount of deformation of the base 230 after application of the cover layer 234. In addition, in some implementations, the materials used to construct the base 230 and the cover layer 234 can be moisture resistant material resulting in the creation of an environment for a vaporizer cartridge that is impervious to moisture and oxygen intrusion, which can impart a beneficial effect on the life of the vaporizer cartridge stored within the cartridge pack cavities 232. In some implementations, the vaporizer cartridge can be stored in cartridge pack cavities 232 in an upright position during shipment and in a retail setting, which can lessen the likelihood of vaporizable material leakage.

FIG. 2C, illustrates a side cross-sectional view of the cartridge packaging 200 as viewed from line 2C-2C in FIG. 2B. As shown in FIG. 2C, the cartridge packaging 200 may include a cover layer 234 applied to the bottom surface of the base 230. Each of the plurality of cartridge pack cavities 232 and/or the void cavity 250 may be recessed from the base 230 to form cavity interior sections 252. A cartridge pack cavity interior section 252a may be sized and configured to contain one vaporizer cartridge of the plurality of vaporizer cartridges. The cartridge pack cavity interior section 252a of at least one of the plurality of cartridge pack cavities 232 may have a squared shape. In some implementations, the void cavity 250 may have a shape such that the center of the void cavity 250 indents toward the base 230 creating a void cavity interior section 252b. As shown in FIG. 2C, the void cavity interior section 252b can be recessed almost entirely to the plane of base 230.

Figure 3A:
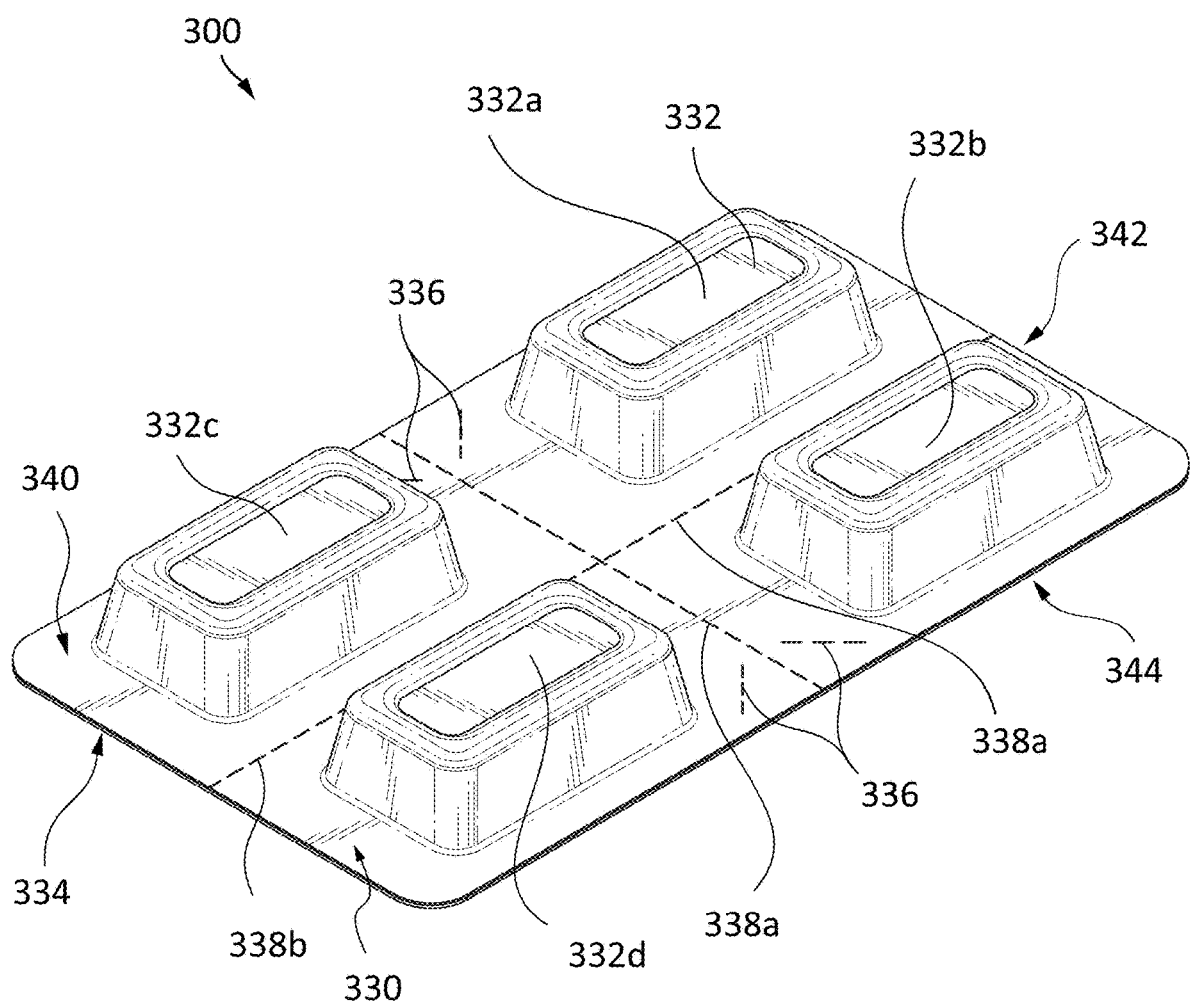
FIG. 3A illustrates a top perspective view of an embodiment of a four-pack cartridge packaging, consistent with implementations of the current subject matter.
Figure 3B:
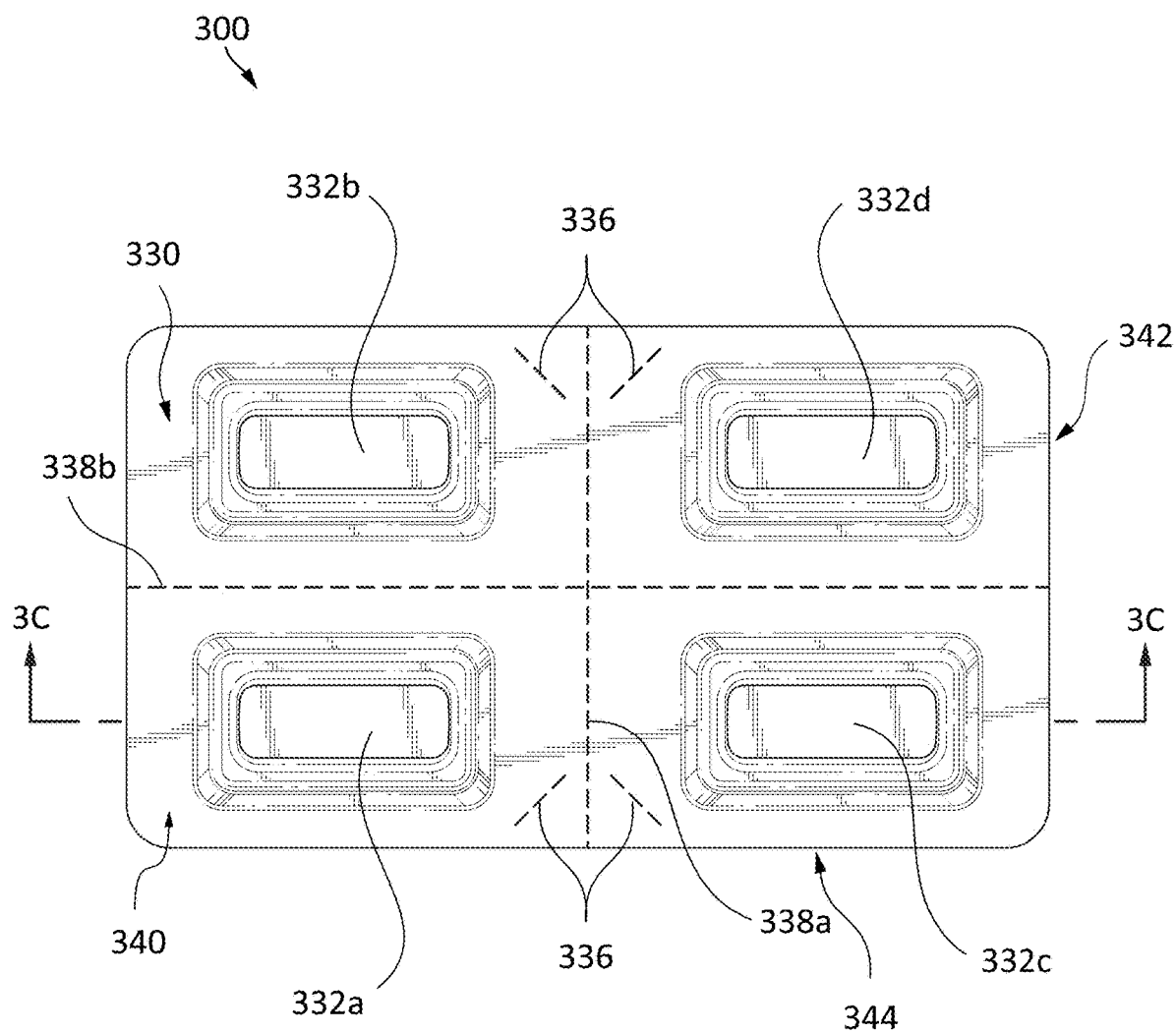
FIG. 3B illustrates a top view of the cartridge packaging embodiment of FIG. 3A.
Figure 3C:
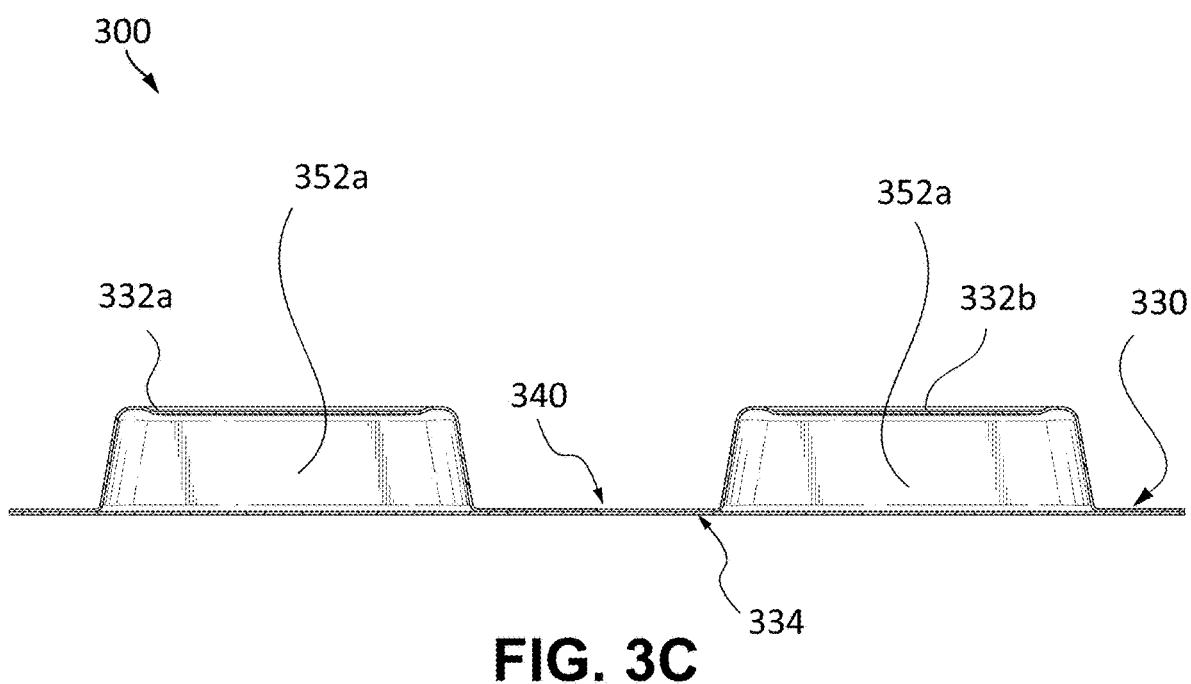
FIG. 3C illustrates a side cross-sectional view of the cartridge packaging embodiment of FIG. 3A.

FIGS. 3A-3C illustrate another embodiment of a cartridge packaging 300 which includes four cartridge pack cavities 332, including a first cartridge pack cavity 332a, a second cartridge pack cavity 332b, a third cartridge pack cavity 332c, and a fourth cartridge pack cavity 332d. Such cartridge pack cavities 332 can include the same or similar features as described above, such as with respect to the cartridge pack cavities 232 of FIGS. 2A-2C. In some implementations, each of the plurality of cartridge pack cavities 332 can be configured to hold a substantially rectangular vaporizer cartridge, such as vaporizer cartridge 120 shown in FIGS. 1A and 1B. Each of the features and functions described above in connection with cartridge packaging 200 of FIGS. 2A-2C can apply to the cartridge packaging 300 embodiment illustrated in FIGS. 3A-3C.

As shown in FIGS. 3A and 3B, the first cartridge pack cavity 332a and the second cartridge pack cavity 332b can be separated by a first perforation 338a. The first perforation 338a can also separate the third cartridge pack cavity 332c from the fourth cartridge pack cavity 332d. The first cartridge pack cavity 332a and the third cartridge pack cavity 332c can be separated by a second perforation 338b. The second perforation 338b can separate the second cartridge pack cavity 332b from the fourth cartridge pack cavity 332d.

The plurality of cartridge pack cavities 332 can include one or more peel-off perforation areas 336. The peel-off perforation areas 336 can be configured to facilitate the opening of each of the plurality of cartridge pack cavities to access the vaporizer cartridge as described above.

FIG. 3C illustrates a side cross-sectional view of the cartridge packaging 300 as viewed from line 3C-3C in FIG. 3B.

Figure 4A:
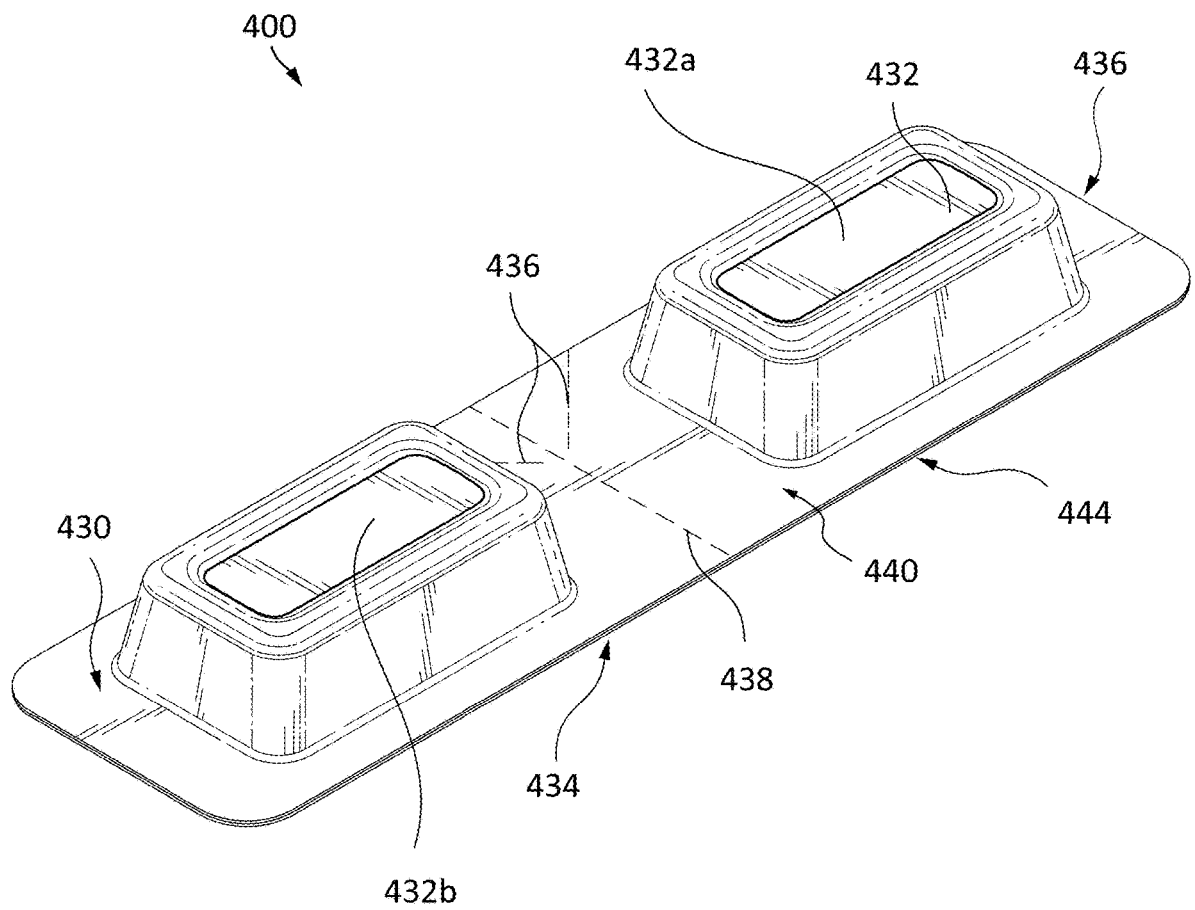
FIG. 4A illustrates a top perspective view of an embodiment of a two-pack cartridge packaging, consistent with implementations of the current subject matter.
Figure 4B:
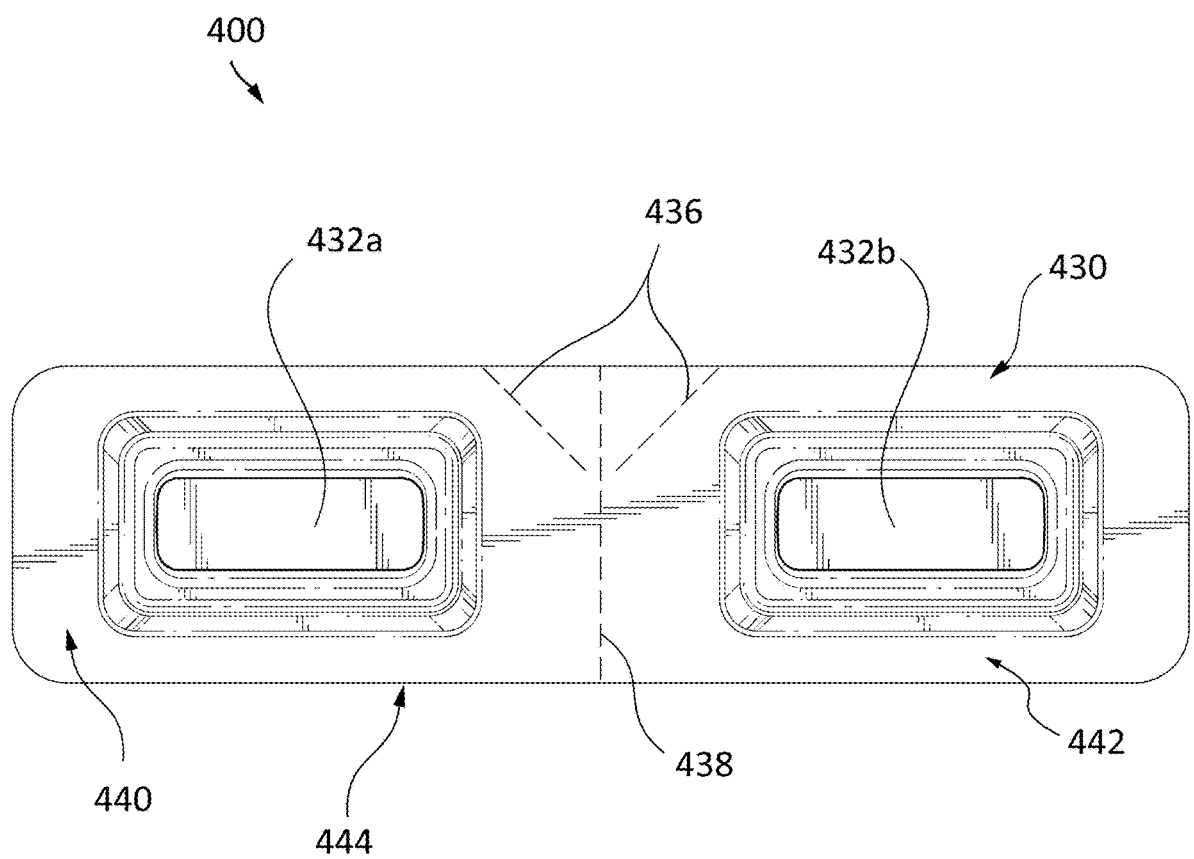
FIG. 4B illustrates a top view of the cartridge packaging embodiment of FIG. 4A.

FIGS. 4A and 4B illustrate another embodiment of a cartridge packaging 400, which includes two cartridge pack cavities 432, including a first cartridge pack cavity 432a and a second cartridge pack cavity 432b. Such cartridge pack cavities 432 can include the same or similar features as described above, such as with respect to the cartridge pack cavities 232 of FIGS. 2A-2C. In some implementations, each of the plurality of cartridge pack cavities 432 can be configured to hold a vaporizer cartridge, such as the vaporizer cartridge 120 shown in FIGS. 1A and 1B. Each of the features as described above in connection with cartridge packaging 200 of FIGS. 2A-2C can apply to the cartridge packaging 400 embodiment of FIGS. 4A and 4B.

As shown in FIGS. 4A and 4B, the first cartridge pack cavity 432a and the second cartridge pack cavity 432b can be separated by a perforation 438.

Figure 5A:
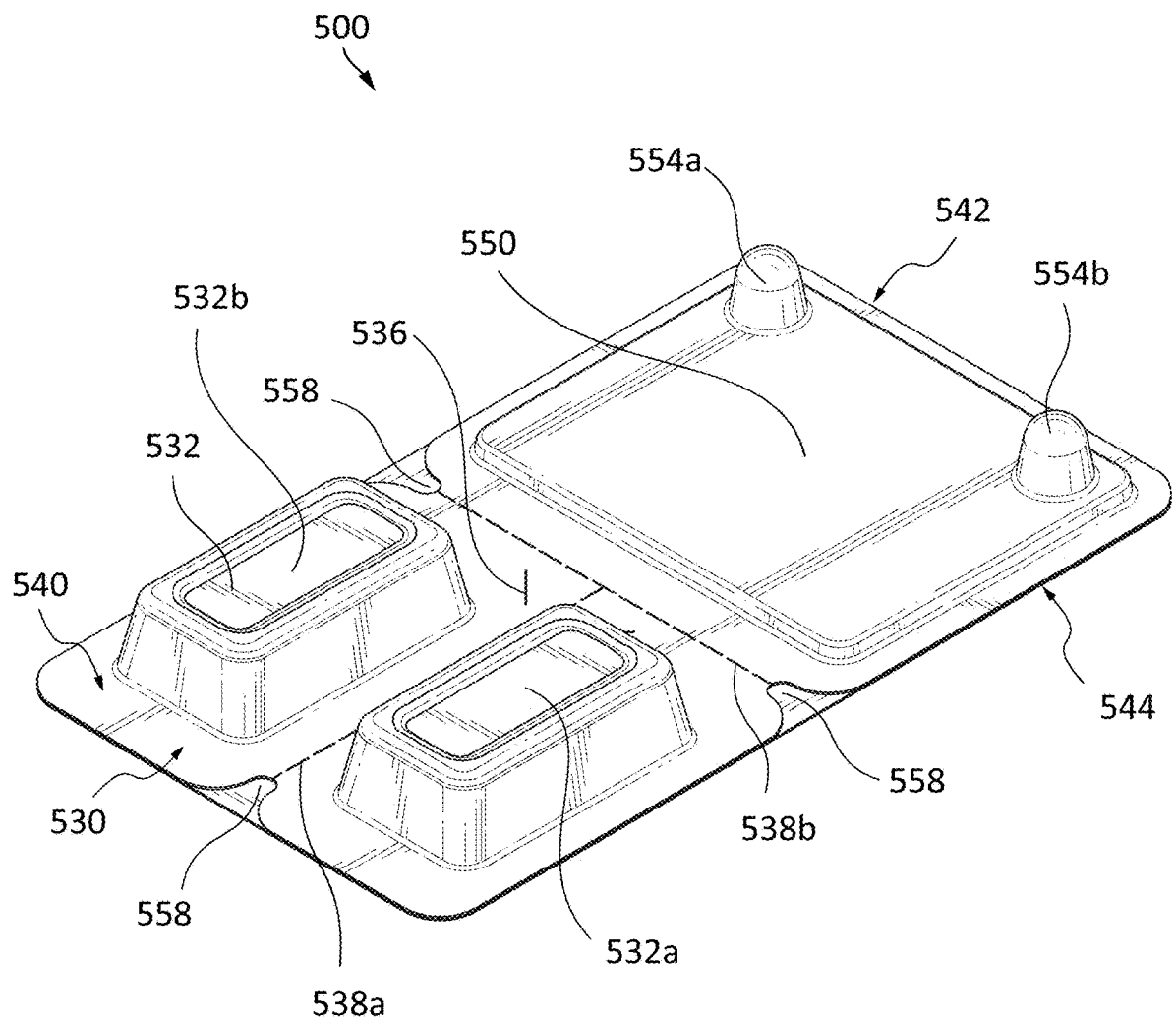
FIG. 5A illustrates a top perspective view of an embodiment of a two-pack cartridge packaging, consistent with implementations of the current subject matter.
Figure 5B:
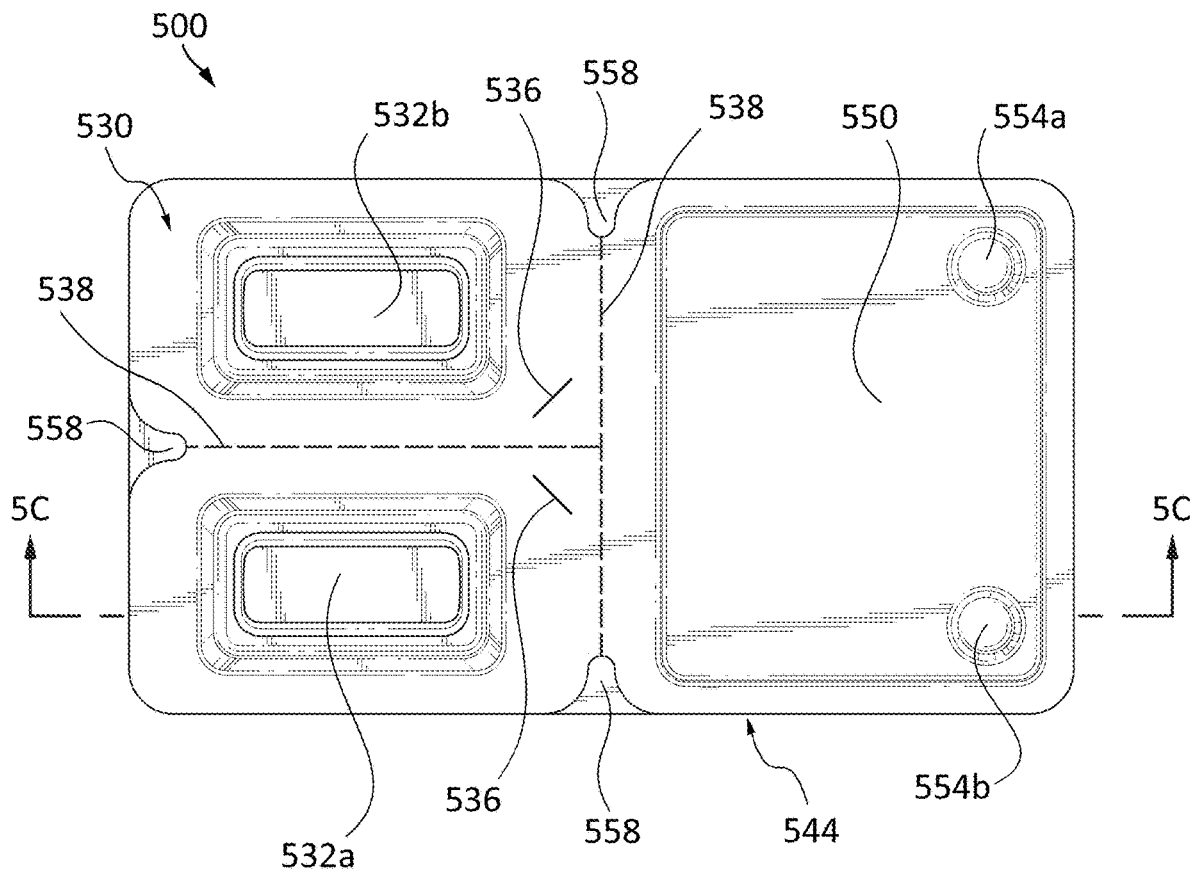
FIG. 5B illustrates a top view of the cartridge packaging embodiment of FIG. 5A.

FIGS. 5A and 5B illustrate another embodiment of a cartridge packaging 500, which includes two cartridge pack cavities 532, including a first cartridge pack cavity 532a and a second cartridge pack cavity 532b. Such cartridge pack cavities 532 can include the same or similar features as described above, such as with respect to the cartridge pack cavities 232 of FIGS. 2A-2C. In some implementations, each of the plurality of cartridge pack cavities 532 can be configured to hold a vaporizer cartridge, such as vaporizer cartridge 120 shown in FIGS. 1A and 1B. Each of the features as described above in connection with cartridge packaging 200 of FIGS. 2A-2C can apply to the cartridge packaging 500 embodiment in FIGS. 5A and 5B.

Figure 5C:
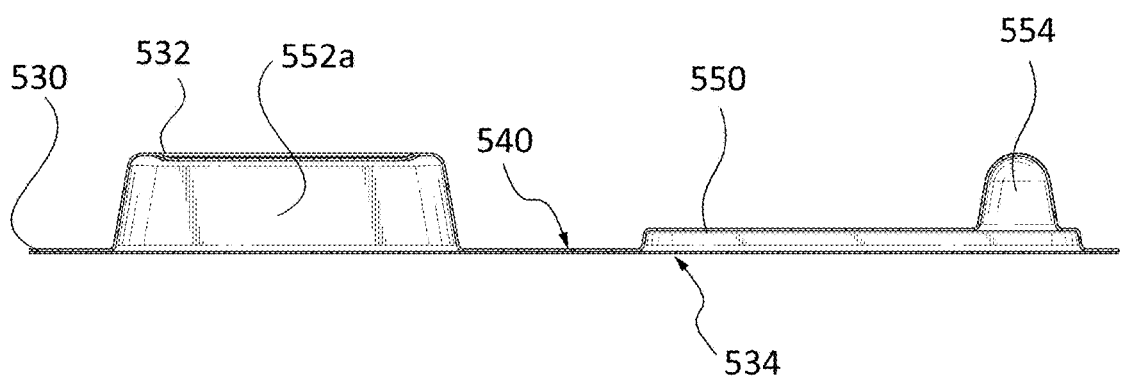
FIG. 5C illustrates a side cross-sectional view of the cartridge packaging embodiment of FIG. 5A.

As shown in FIGS. 5A-5C, cartridge packaging 500 can include a void cavity 550. The void cavity 550 can include the same or similar features as described above, such as with respect to the void cavity 250 of FIGS. 2A-2C. The void cavity 550 may include a substantially flat region adjacent to one or more protrusion features 554, such as a first protrusion feature 554a and a second protrusion feature 554b. The protrusion features 554 may be configured to increase stiffness of the cartridge packaging 500. As shown in FIG. 5C, the protrusion features 554 may have a height/depth that is the same as or substantially similar to the depth of the cartridge pack cavities 532 to thereby provide a uniform height/depth to the cartridge packaging 500. This can allow for efficient and effective loading of the cartridge packaging into a storage compartment, such as a carton, for shipping to consumers and storage. One or more perforations 538 may include corresponding notches 558 adjacent to the edge of the base 530 to aid in initiating tearing of the base 530 along the perforations 538.

FIG. 5C illustrates a side cross-sectional view of the cartridge packaging 500 as viewed from line 5C-5C in FIG. 5B.

Figure 6A:
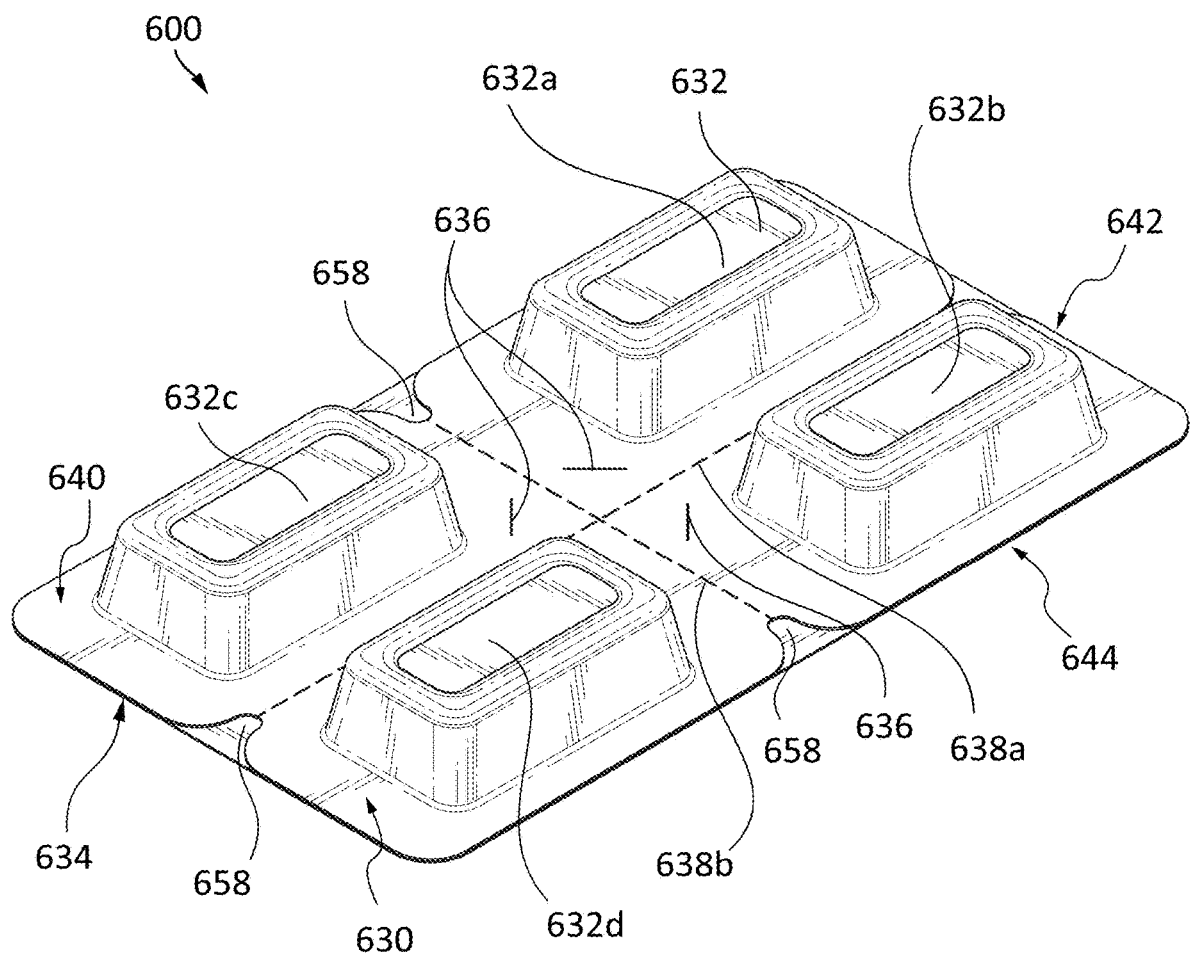
FIG. 6A illustrates a top perspective view of an embodiment of a four-pack cartridge packaging, consistent with implementations of the current subject matter.
Figure 6B:
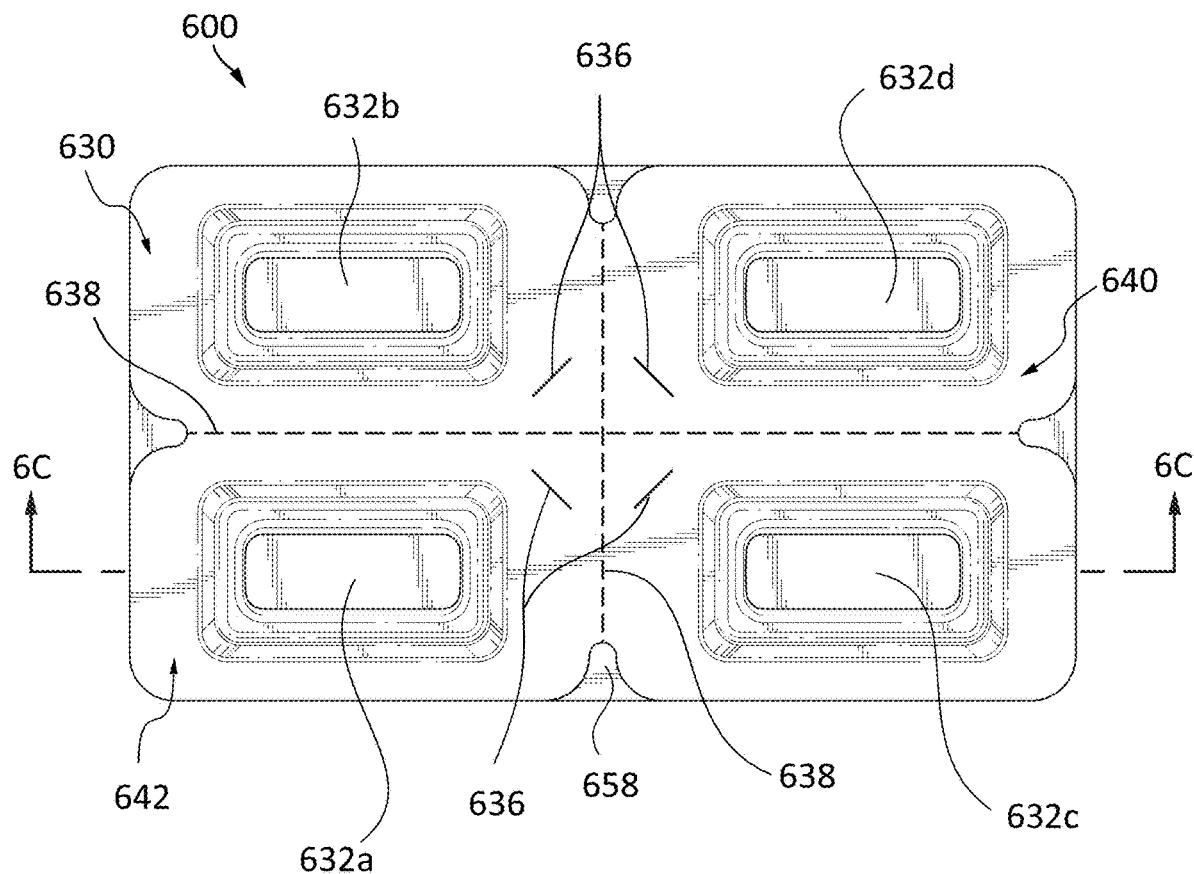
FIG. 6B illustrates a top view of the cartridge packaging embodiment of FIG. 6A.

As shown in FIGS. 6A and 6B, the first cartridge pack cavity 632a and the second cartridge pack cavity 632b can be separated by a first perforation 638a. The first perforation 638a can also separate the third cartridge pack cavity 632c from the fourth cartridge pack cavity 632d. The first cartridge pack cavity 632a and the third cartridge pack cavity 632c can be separated by a second perforation 638b. The second perforation 638b can separate the second cartridge pack cavity 632*b* from the fourth cartridge pack cavity 632*d*. The perforations 638 may include corresponding notches 658 adjacent to the edge of the base 630 to aid in initiating tearing of the base 630 along the perforations 638.

Figure 6C:
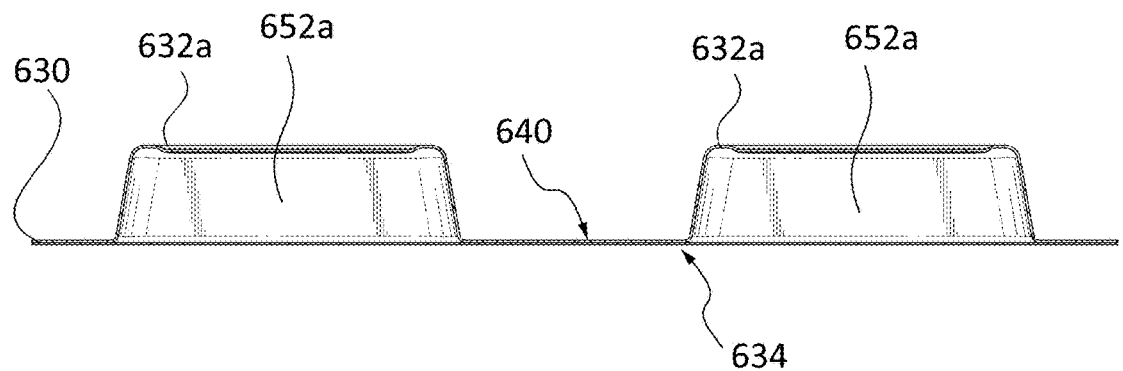
FIG. 6C illustrates a side cross-sectional view of the cartridge packaging embodiment of FIG. 6A.

FIG. 6C illustrates a side cross-sectional view of the cartridge packaging 600 as viewed from line 6C-6C in FIG. 6B.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A cartridge packaging for containing a plurality of cartridges for a vaporizer device, the cartridge packaging comprising:
    a base that extends in at least a vertical dimension and a horizontal dimension;
    a first cartridge pack cavity and a second cartridge pack cavity formed within the base, the first cartridge pack cavity and the second cartridge pack cavity adjacent to each other along the vertical dimension and separated by one or more vertical perforations extending through the base, the one or more vertical perforations being provided along at least part of the horizontal dimension of the base, each of the first cartridge pack cavity and the second cartridge pack cavity being sized and configured to contain one cartridge of the plurality of cartridges, and each of the first cartridge pack cavity and the second cartridge pack cavity having a first depth; and
    a void cavity formed within the base and configured to reduce deformation of the base, the void cavity adjacent to each of the first cartridge pack cavity and the second cartridge pack cavity along the horizontal dimension, the void cavity being separated from the first cartridge pack cavity and the second cartridge pack cavity by one or more horizontal perforations in the base, the one or more horizontal perforations being provided along at least part of the vertical dimension of the base, and the void cavity having a second depth that is approximately the same as the first depth of the first cartridge pack cavity and the second cartridge pack cavity;
    wherein the void cavity comprises a first section that extends from the second depth and towards a center of the void cavity, and wherein the first section surrounds the center of the void cavity and defines an interior section that includes the center of the void cavity.

2. The cartridge packaging in accordance with claim 1, further comprising a cover layer applied to at least a portion of the base to seal at least the first cartridge pack cavity, the second cartridge pack cavity, and the void cavity.

3. The cartridge packaging in accordance with claim 2, wherein the cover layer comprises a breakable material that, when broken proximate the first cartridge pack cavity or the second cartridge pack cavity, allows release of a cartridge of the plurality of cartridges contained within the first cartridge pack cavity or the second cartridge pack cavity.

4. The cartridge packaging in accordance with claim 1, further comprising one or more peel-off perforations proximate to each of the first cartridge pack cavity and the second cartridge pack cavity.

5. The cartridge packaging in accordance with claim 4, wherein the one or more peel-off perforations extend in a direction that is from the one or more horizontal perforations and towards an edge of the base that is along the horizontal dimension.

6. The cartridge packaging in accordance with claim 1, wherein the one or more vertical perforations and the one or more horizontal perforations allow for removal of the first cartridge pack cavity, the second cartridge pack cavity, and/or the void cavity from a remainder of the base.

7. A cartridge packaging, comprising:
a base that extends in at least a vertical dimension and a horizontal dimension;
a plurality of cartridge pack cavities formed within the base, the plurality of cartridge pack cavities comprising a first cartridge pack cavity and a second cartridge pack cavity, the first cartridge pack cavity being separated from the second cartridge pack cavity by one or more vertical perforations extending through the base, the one or more vertical perforations being provided along at least part of the horizontal dimension of the base, each of the plurality of cartridge pack cavities having a respective cartridge disposed therein, each cartridge having a vaporizable material housed therein; and
a void cavity formed within the base and configured to reduce deformation of the base, the void cavity adjacent to the plurality of cartridge pack cavities, the void cavity being separated from the plurality of cartridge pack cavities by one or more horizontal perforations in the base, the one or more horizontal perforations being provided along at least part of the vertical dimension of the base, and each of the plurality of cartridge pack cavities and the void cavity having approximately the same depth,
wherein the void cavity comprises a first section that extends from a depth of the void cavity and towards a center of the void cavity, and wherein the first section surrounds the center of the void cavity and defines an interior section that includes the center of the void cavity.

8. The cartridge packaging in accordance with claim 7, further comprising a cover layer applied to at least a portion of the base to seal each of the plurality of cartridge pack cavities and the void cavity.

9. The cartridge packaging in accordance with claim 8, wherein the cover layer comprises a breakable material that, when broken allows release of a cartridge of the plurality of cartridges contained within one of the plurality of cartridge pack cavities.

10. The cartridge packaging in accordance with claim 9, wherein the one or more vertical perforations and the one or more horizontal perforations allow for removal of each of the plurality of cartridge pack cavities and/or the void cavity from a remainder of the base.

11. The cartridge packaging in accordance with claim 7, wherein at least one of the plurality of cartridge pack cavities has a squared or rectangular shape.

12. The cartridge packaging in accordance with claim 7, further comprising one or more peel-off perforations proximate to each of the plurality of cartridge pack cavities.

13. The cartridge packaging in accordance with claim 12, wherein the one or more peel-off perforations extend in a direction that is from the one or more horizontal perforations and towards an edge of the base that is along the horizontal dimension.

14. The cartridge packaging in accordance with claim 7, wherein the vaporizable material comprises nicotine.

15. A cartridge packaging for containing a plurality of cartridges for a vaporizer device, the cartridge packaging comprising:
a base that extends in at least a vertical dimension and a horizontal dimension;
a plurality of cartridge pack cavities formed within the base, each of the plurality of cartridge pack cavities being separated from another cartridge pack cavity by one or more vertical perforations extending through the base, the one or more vertical perforations being provided along at least part of the horizontal dimension of the base, each of the plurality of cartridge pack cavities being sized and configured to contain one cartridge of the plurality of cartridges;
a void cavity formed within the base and configured to reduce deformation of the base, the void cavity adjacent to the plurality of cartridge pack cavities, the void cavity being separated from the plurality of cartridge pack cavities by one or more horizontal perforations in the base, the one or more horizontal perforations being provided along at least part of the vertical dimension of the base, and each of the plurality of cartridge pack cavities and the void cavity having approximately the same depth; and
a cover layer applied to the base, the cover layer providing an airtight seal to each of the plurality of cartridge pack cavities when applied to the base,
wherein the void cavity comprises a first section that extends, from the depth of the void cavity, towards a center of the void cavity and towards the cover layer, and wherein the first section surrounds the center of the void cavity and defines an interior section that includes the center of the void cavity.

16. The cartridge packaging in accordance with claim 15, wherein the cover layer comprises a breakable material that, when broken proximate one of the plurality of cartridge pack cavities, allows release of a cartridge of the plurality of cartridges contained within one of the plurality of cartridge pack cavities.

17. The cartridge packaging in accordance with claim 15, wherein at least one of the plurality of cartridge pack cavities has a squared or rectangular shape.

18. The cartridge packaging in accordance with claim 15, further comprising one or more peel-off perforations proximate to each of the plurality of cartridge pack cavities.

19. The cartridge packaging in accordance with claim 18, wherein the one or more peel-off perforations extend in a direction that is from the one or more horizontal perforations and towards an edge of the base that is along the horizontal dimension.

20. The cartridge packaging in accordance with claim 15, wherein the one or more vertical perforations and the one or more horizontal perforations allow for removal of each of the plurality of cartridge pack cavities and/or the void cavity from a remainder of the base.

21. The cartridge packaging in accordance with claim 15, wherein the cover layer is applied to a portion of the first section.

* * * * *